(12) United States Patent
Nazari et al.

(10) Patent No.: US 10,788,407 B2
(45) Date of Patent: Sep. 29, 2020

(54) EMULSION COMPOSITION SENSOR

(71) Applicant: NEXEN ENERGY ULC, Calgary (CA)

(72) Inventors: Alireza Nazari, Calgary (CA); Yiming Ji, Calgary (CA); Daniel Joseph Giesbrecht, Calgary (CA)

(73) Assignee: CNOOC PETROLEUM NORTH AMERICA ULC, Calgary (CA)

(*) Notice: Subject to any disclaimer, the term of this patent is extended or adjusted under 35 U.S.C. 154(b) by 270 days.

(21) Appl. No.: 15/769,837

(22) PCT Filed: Oct. 28, 2016

(86) PCT No.: PCT/CA2016/051252
§ 371 (c)(1),
(2) Date: Apr. 20, 2018

(87) PCT Pub. No.: WO2017/070789
PCT Pub. Date: May 4, 2017

(65) Prior Publication Data
US 2018/0306693 A1   Oct. 25, 2018

Related U.S. Application Data

(60) Provisional application No. 62/247,815, filed on Oct. 29, 2015.

(51) Int. Cl.
*G01N 9/36* (2006.01)
*G01N 11/02* (2006.01)
(Continued)

(52) U.S. Cl.
CPC ............ *G01N 9/36* (2013.01); *E21B 47/008* (2020.05); *E21B 47/06* (2013.01); *E21B 47/07* (2020.05);
(Continued)

(58) Field of Classification Search
USPC .......................................................... 702/12
See application file for complete search history.

(56) References Cited

U.S. PATENT DOCUMENTS 5,222,867 A * 6/1993 Walker, Sr. ......... E21B 47/0008
417/12
7,081,615 B2   7/2006 Betancourt et al.
(Continued)

FOREIGN PATENT DOCUMENTS

CN         104563927 A      4/2015

OTHER PUBLICATIONS

International Searching Authority, International Search Report and Written Opinion issued in International Application No. PCT/CA2016/051252 dated Jan. 26, 2017.

*Primary Examiner* — Paul D Lee
(74) *Attorney, Agent, or Firm* — Norton Rose Fulbright Canada LLP

(57) ABSTRACT

A system for sensing an estimated composition of a produced fluid being conducted from a reservoir includes: at least one device for measuring temperature data; at least one device for obtaining flow rate data, pressure data, pump speed data and valve travel data; a first produced fluid density generator; a second produced fluid density generator; and a composition generator. The first produced fluid density generator is configured to generate a first produced fluid density based on the obtained flow rate, pressure, pump speed and valve travel data. The second produced fluid density generator is configured to generate a second produced fluid density based at least in part on the measured temperature data. The composition generator is configured to: iteratively generate a phantom component content, a bitumen content and a water content for the produced fluid based on at least in part on: a material balance of the produced fluid.

20 Claims, 19 Drawing Sheets

(51) Int. Cl.
*G06N 3/08* (2006.01)
*E21B 47/07* (2012.01)
*E21B 47/008* (2012.01)
*E21B 47/06* (2012.01)
*E21B 47/10* (2012.01)
*E21B 49/08* (2006.01)
*G01N 33/28* (2006.01)
*E21B 49/00* (2006.01)
*G06N 3/04* (2006.01)
*E21B 43/24* (2006.01)

(52) U.S. Cl.
CPC .............. *E21B 47/10* (2013.01); *E21B 49/08* (2013.01); *G01N 11/02* (2013.01); *G01N 33/2847* (2013.01); *G06N 3/08* (2013.01); *E21B 43/2406* (2013.01); *E21B 49/00* (2013.01); *E21B 49/0875* (2020.05); *G01N 33/28* (2013.01); *G06N 3/0472* (2013.01)

(56) References Cited

U.S. PATENT DOCUMENTS

| | | | |
|---|---|---|---|
| 8,805,617 B2* | 8/2014 | Zuo | E21B 49/10 702/11 |
| 2011/0185809 A1* | 8/2011 | Guieze | G01N 1/2202 73/32 R |
| 2011/0246143 A1* | 10/2011 | Pomerantz | E21B 49/00 703/2 |
| 2012/0000658 A1 | 1/2012 | Coludrovich, III et al. | |
| 2012/0296617 A1* | 11/2012 | Zuo | E21B 49/082 703/10 |
| 2014/0262516 A1* | 9/2014 | Larson | G01N 33/2823 175/48 |
| 2015/0081265 A1 | 3/2015 | Kauerauf et al. | |

* cited by examiner

EMULSION COMPOSITION SENSOR

CROSS-REFERENCE TO RELATED APPLICATIONS

The present disclosure claims all benefit, including priority, of U.S. Provisional Patent Application 62/247,815, filed Oct. 29, 2015, and entitled "EMULSION COMPOSITION SENSOR", the entirety of which, including appendices, is hereby incorporated by reference.

FIELD

The present disclosure generally relates to the field of hydrocarbon recovery and in particular to systems, devices and methods for estimating emulsion composition in a hydrocarbon recovery process.

INTRODUCTION

Emulsion streams in hydrocarbon recover processes can consist of different components including bitumen, water, gases, and solids. Samples of the emulsion streams can be taken for laboratory analysis to determine the composition of the emulsion stream at the time of sampling. However, the laboratory analysis can take days to complete.

It would be beneficial to estimate the composition of an emulsion stream more quickly.

SUMMARY

In accordance with one aspect, there is provided a system for sensing an estimated composition of a produced fluid being conducted from a reservoir. The system includes at least one device for measuring temperature data for the produced fluid; at least one device for obtaining flow rate data, pressure data, pump speed data and valve travel data for the produced fluid being conducted from the reservoir; at least one memory device for storing obtained and historical data; a first produced fluid density generator; a second produced fluid density generator; and a composition generator. The first produced fluid density generator is configured to generate a first produced fluid density based at least in part on the obtained flow rate data, pressure data, pump speed data and valve travel data for the produced fluid being conducted from the reservoir. The second produced fluid density generator is configured to generate a second produced fluid density based at least in part on a bitumen reference density corresponding to the measured temperature data, a water reference density corresponding to the measured temperature data, and a phantom component reference density corresponding to the measured temperature data. The composition generator is configured to: generate, with an iterative convergence tool, a phantom component content, a bitumen content and a water content for the produced fluid based on at least in part on: a material balance of the produced fluid and a difference between the first produced fluid density and the second produced fluid density; and generate outputs representing the phantom component content, the bitumen content and the water content.

In accordance with another aspect, there is provided a method for sensing an estimated composition of a produced fluid being conducted from a reservoir. The method includes: measuring, with at least one sensing device, temperature data for the produced fluid; obtaining, with the at least one sensing device, flow rate data, pressure data, pump speed data and valve travel data for the produced fluid being conducted from the reservoir; generating a first produced fluid density based at least in part on the obtained flow rate data, pressure data, pump speed data and valve travel data for the produced fluid being conducted from the reservoir; generating a second produced fluid density based at least in part on a bitumen reference density corresponding to the measured temperature data, a water reference density corresponding to the measured temperature data, and a phantom component reference density corresponding to the measured temperature data; generating, with an iterative convergence tool, a phantom component content, a bitumen content and a water content for the produced fluid based on at least in part on: a material balance of the produced fluid and a difference between the first produced fluid density and the second produced fluid density; and generating outputs representing the phantom component content, the bitumen content and the water content.

In accordance with another aspect, there is provided a non-transitory, computer-readable medium or media having stored thereon instructions which when executed by at least one processor configure the at least one processor for: measuring, with at least one sensing device, temperature data for the produced fluid; obtaining, with the at least one sensing device, flow rate data, pressure data, pump speed data and valve travel data for the produced fluid being conducted from the reservoir; generating a first produced fluid density based at least in part on the obtained flow rate data, pressure data, pump speed data and valve travel data for the produced fluid being conducted from the reservoir; generating a second produced fluid density based at least in part on a bitumen reference density corresponding to the measured temperature data, a water reference density corresponding to the measured temperature data, and a phantom component reference density corresponding to the measured temperature data; generating, with an iterative convergence tool, a phantom component content, a bitumen content and a water content for the produced fluid based on at least in part on: a material balance of the produced fluid and a difference between the first produced fluid density and the second produced fluid density; and generating outputs representing the phantom component content, the bitumen content and the water content.

DETAILED DESCRIPTION

Wellhead produced fluid (e.g. emulsion) primarily consists of water and bitumen so physical properties of these two components could be used to generate emulsion composition estimates. However, unlike the composition and physical properties of water which do not significantly change during the course of operation of a hydrocarbon recovery system such as a SAGD (steam assisted gravity drainage) system, those of bitumen may change as the production reservoir matures. More specifically, in some instances, bitumen have been observed to become lighter as a SAGD reservoir ages. In addition, produced fluid may be contaminated with free gas and/or solid particles which may cause a sometimes significant change in the produced fluid's physical properties.

The present disclosure describes systems, devices, and methods for estimating produced fluid compositions which may, in some embodiments, account for one or more of these dynamic produced fluid characteristics. In some embodiments, aspects of the present disclosure may estimate produced fluid compositions based on sensor or other input device data while addressing variations in the produced fluid flow.

In some embodiments, the system is configured to generate and output signals identifying the produced fluid as being a clean emulsion, as including solids, and/or as including gas. Flow and Coriolis meters are generally not able to provide an indication of the presence of solids or gas in the production line. As these can potentially cause damage to pump or meters, or may be generally undesirable, in some embodiments, the system can generate alerts as to the presence of solids or gas in the produced fluid being conducted from the reservoir.

In some embodiments, the system may be configured to generate an alert if the composition indicates that there is too much water or steam in the produced fluid as this may be indicative of breakthrough or insufficient injection well pressure.

In some embodiments, outputs the methods and systems described herein may be used to calibrate or otherwise monitor the outputs of one or more meters in the system.

Figure 1A:
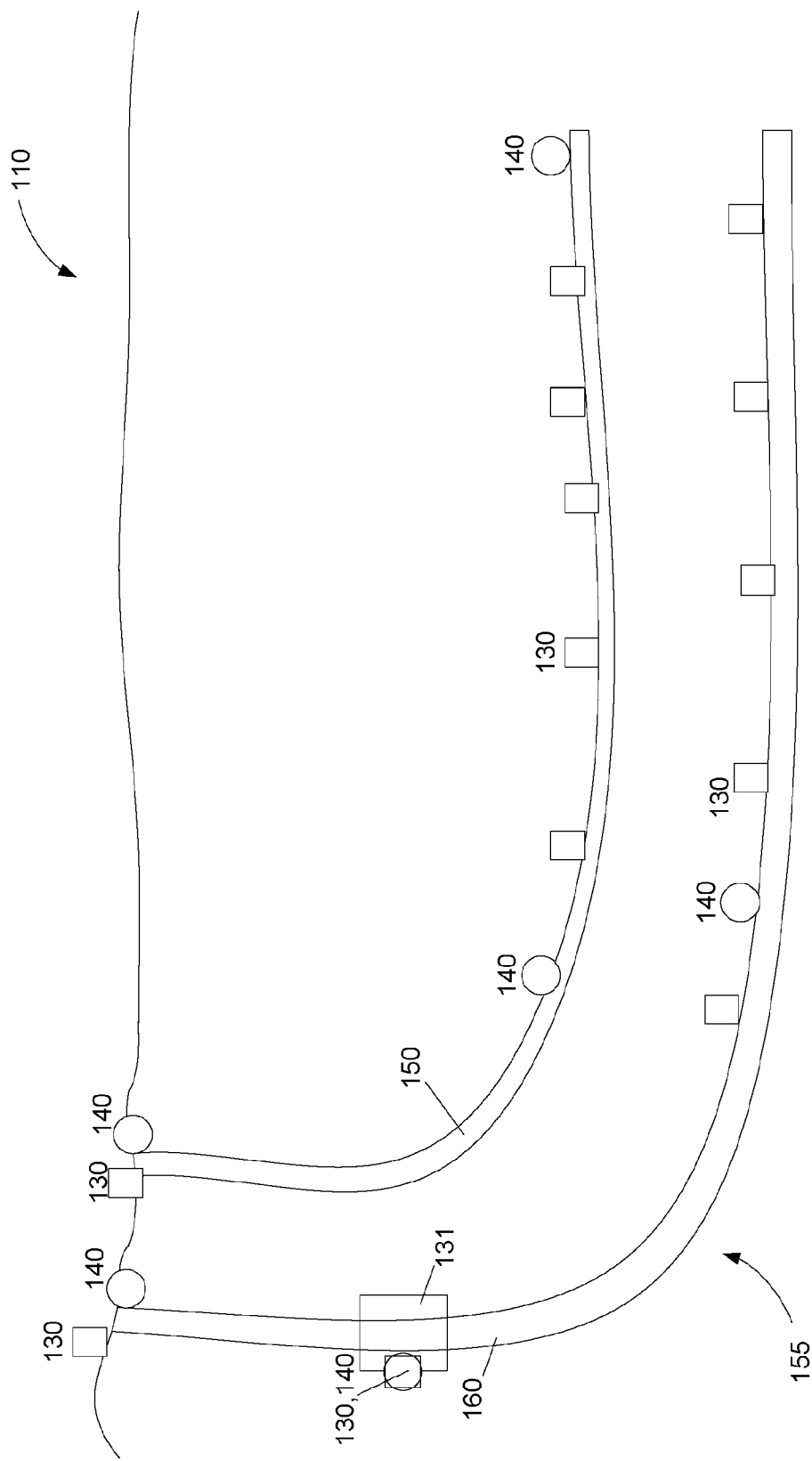
FIG. 1A is a cross sectional view of an example geological formation and SAGD well.

FIG. 1A shows an example of a steam assisted gravity drainage (SAGD) well 155 in a geological resource 110. In SAGD, production is typically effected by a pair of wells 155: an injector well 150 for injecting steam and/or other production inducing material into the geological formation, and a producer well 160 for collecting the resulting bitumen.

Figure 1B:
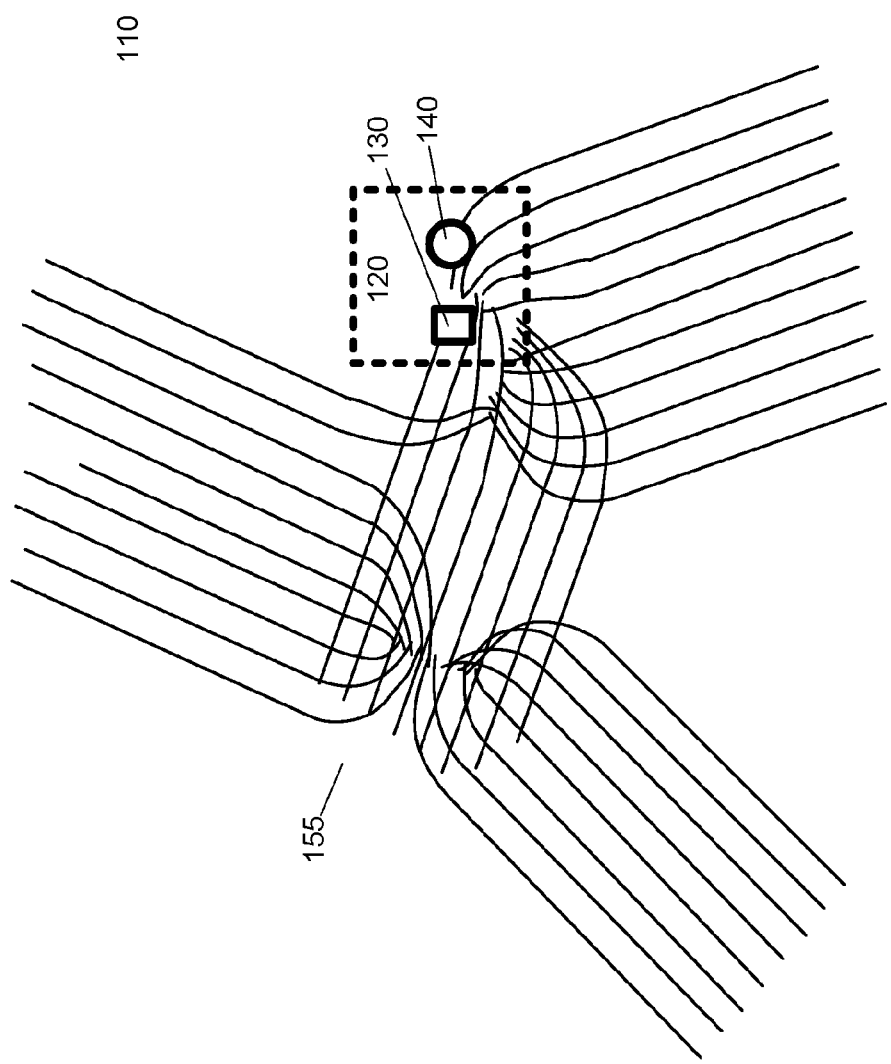
FIG. 1B is a top view of a geological area illustrating SAGD wells and infrastructure for an example project.

FIG. 1B shows a top elevation view of a geological resource 110 having many wells (pairs) 155. The well(s) may be part of one or more SAGD projects for extracting the hydrocarbon resources in the geological formation. As illustrated by the example project in FIG. 1B, these projects may have any number of wells 155 having any number of orientations and locations. The project(s) may include one or more facilities 120 such as well pads, plants, water sources, control systems, monitoring systems, steam generators, upgraders and any other infrastructure for extracting and/or processing input and output materials.

The systems in FIGS. 1A and 1B show example steam-assisted gravity drainage (SADG) systems; however, in other embodiments, aspects of the present disclose may be applied to other systems involving single wells or other different hydrocarbon recovery processes.

The wells and/or infrastructure can include one or more input devices 130 for measuring, detecting or otherwise collecting data regarding the wells and processes. This data can, in some examples, include well conditions and output or production rates.

In some examples, the input devices 130 can include thermocouples or other temperature sensors, pressure sensors, and the like for measuring temperature, pressure and/or other conditions within the wells, proximate to the wells, and/or at the surface. In some examples, multiple input devices can be positioned along the length of the wells to measuring well conditions at various points in or around the length of the wells. For example, pressure and/or temperature sensors may be positioned at the toe of the well, the heel of the well, at the surface and/or elsewhere in the project infrastructure. In some examples, input sensors from reference wells, surrounding production wells, or other wells may also provide well condition information for a proximate well.

In some examples, inputs devices 130 may include flow sensors at the surface, at positions along the well and/or within any other project infrastructure to provide flow information and/or bitumen production rates. In some examples, input devices 130 can include sensors, measuring devices, and/or computational devices for determining a well's production rates of a desired hydrocarbon after processing and/or removal of water and/or other materials. In some examples, the devices may include flow meters for measuring total fluid extracted from the well.

The wells and/or infrastructure can include one or more control devices 140 for adjusting the operational inputs of the wells. In some examples, these control devices 140 can include valves, pumps, mixers, boilers, nozzles, sliding sleeves, inflow/injection control devices, drives, motors, relays and/or any other devices which may control or affect the operational inputs of the wells. In some examples, these control device(s) 140 may be configured, controlled or otherwise adjusted to change operational inputs via signals or instructions received from one or more processors in the system. For example, one or more of the control devices 140 may include controllers, processors, communication devices, electrical switches and/or other circuitry, devices or logic which can be configured, instructed or otherwise triggered to change operational inputs such as steam injection rates, temperatures, pressures, steam injection locations, pump speeds, water consumption rates, fuel consumption and any other adjustable or controllable aspect of the system. In some examples, one or more of the control devices 140 may be additionally or alternatively controlled by physical mechanisms.

In some embodiments, one or more valves such as a choke valve at the wellhead or elsewhere can include input device(s) 130 which measure or otherwise obtain the travel of a valve stem.

In some embodiments, the input devices 130 may include one or more pressure sensing devices for obtaining emulsion pressure(s) at one or more locations in the process. In some examples, the emulsion pressure can be obtained at a well-pad group separator, at an emulsion header, or at any other point after an emulsion choke valve or elsewhere.

The number and location of the input devices 130 and control devices 140 in FIGS. 1A and 1B are illustrative examples only as any number, location and/or type of these devices 130, 140 is possible.

In some example embodiments, the input devices 130 can include sensing device cables/wires which may run the length of an entire well or portion of a well, and may provide continuous or spaced measurements along the length of the cable/wire.

In some embodiments, the producer well 160 may include a pumping mechanism 131 such as an electrical submersible pump. In some embodiments, the system can include a device for obtaining the speed at which the pumping mechanism is operating. In some examples, this device can be an input device 130 which measures or otherwise obtains the pumping speed. In other examples, this device can be a control device 140 which controls the pumping speed. This speed, whether measured or controlled, can be communicated back to a controller/processor in the system.

Aspects of the devices, systems and methods described herein may be implemented in a combination of both hardware and software. These embodiments may be implemented on programmable computers. One or more computers may include at least one processor, a data storage system (including volatile memory or non-volatile memory or other data storage elements or a combination thereof), and at least one communication interface. In some embodiments, computers can include controller(s), control device(s), data acquisition device(s), and/or any other device for computing or otherwise handling data. Produced fluid density generators, composition generators, and/or produced fluid viscosity generators can be implemented on such hardware or software.

Program code may be applied to input data to perform the functions described herein and to generate output information. The output information may be applied to one or more output or control devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof. In some examples, devices having at least one processor may be configured to execute software instructions stored on a computer readable tangible, non-transitory medium.

The following discussion provides many example embodiments. Although each embodiment represents a single combination of inventive elements, other examples may include all possible combinations of the disclosed elements. Thus if one embodiment comprises elements A, B, and C, and a second embodiment comprises elements B and D, other remaining combinations of A, B, C, or D, may also be used.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

Figure 2:
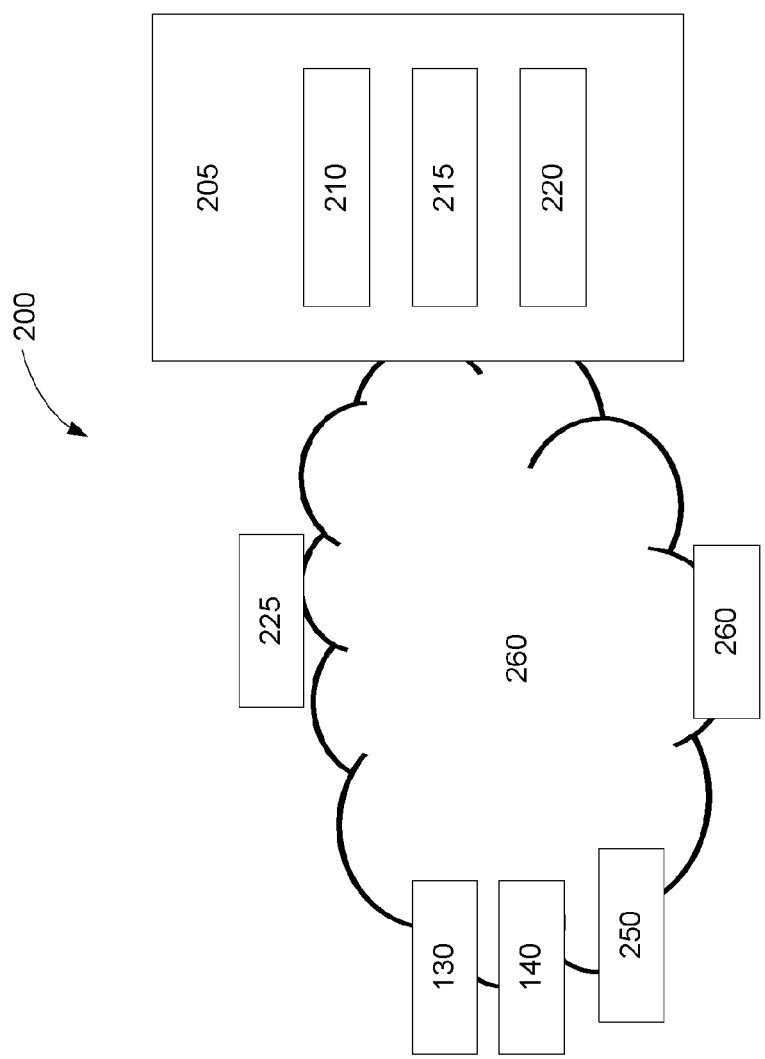
FIG. 2 is an example system to which aspects of the present disclosure may be applied.

FIG. 2 shows an example system 200 including one or more devices 205 which may be used to estimate produced fluid composition. In some examples, a device 205 may be a computational device such as a computer, server, tablet or mobile device, or other system, device or any combination thereof suitable for accomplishing the purposes described herein. In some examples, the device 205 can include one or more processor(s) 210, memories 215, and/or one or more devices/interfaces 220 necessary or desirable for input/output, communications, control and the like. The processor(s) 210 and/or other components of the device(s) 205 or system 250 may be configured to perform one or more aspects of the processes described herein.

In some examples, the device(s) 205 may be configured to receive or access data from one or more volatile or non-volatile memories 215, or external storage devices 225 directly coupled to a device 205 or accessible via one or more wired and/or wireless network(s)/communication link(s) 260. In external storage device(s) 225 can be a network storage device or may be part of or connected to a server or other device.

In some examples, the device(s) 205 may be configured to receive or access data from sensors or input devices 130 in the field or infrastructure. These sensors or devices 130 may be configured for collecting or measuring well, infrastructure, operational, and/or other geological and/or physical data. In some examples, the sensor(s)/device(s) 130 can be configured to communicate the collected data to the device(s) 205 and/or storage device(s) 225 via one or more networks/links 260 or otherwise. In some examples, the sensors or devices 130 may be connected to a local computing device 250 which may be configured to receive the data from the sensors/devices 130 for local storage and/or communication to the device(s) 205 and/or storage device(s) 225. In some examples, data from sensor(s) or device(s) may be manually read from a gauge or dial, and inputted into a local computing device for communication and/or storage.

In some examples, the device(s) 205 may be configured to generate and/or transmit signals or instructions to one or more control device(s) 140 to apply desired operational inputs/conditions to the wells. These signals/instructions may, in some examples, be communicated via any single or combination of networks/links 260. In some examples, the device(s) 205 may be configured to send signals/instructions via local computing device(s) 250 connected to or otherwise in communication with the control device(s) 140. In some examples, a local computing device 250, display or other device may be configured to communicate instructions to a person for manual adjustment/control of the control device(s) 140.

In some examples, a client device 260 may connect to or otherwise communicate with the device(s) 205 to gain access to the data and/or to instruct or request that the device(s) 205 perform some or all of the aspects described herein.

Figure 3:
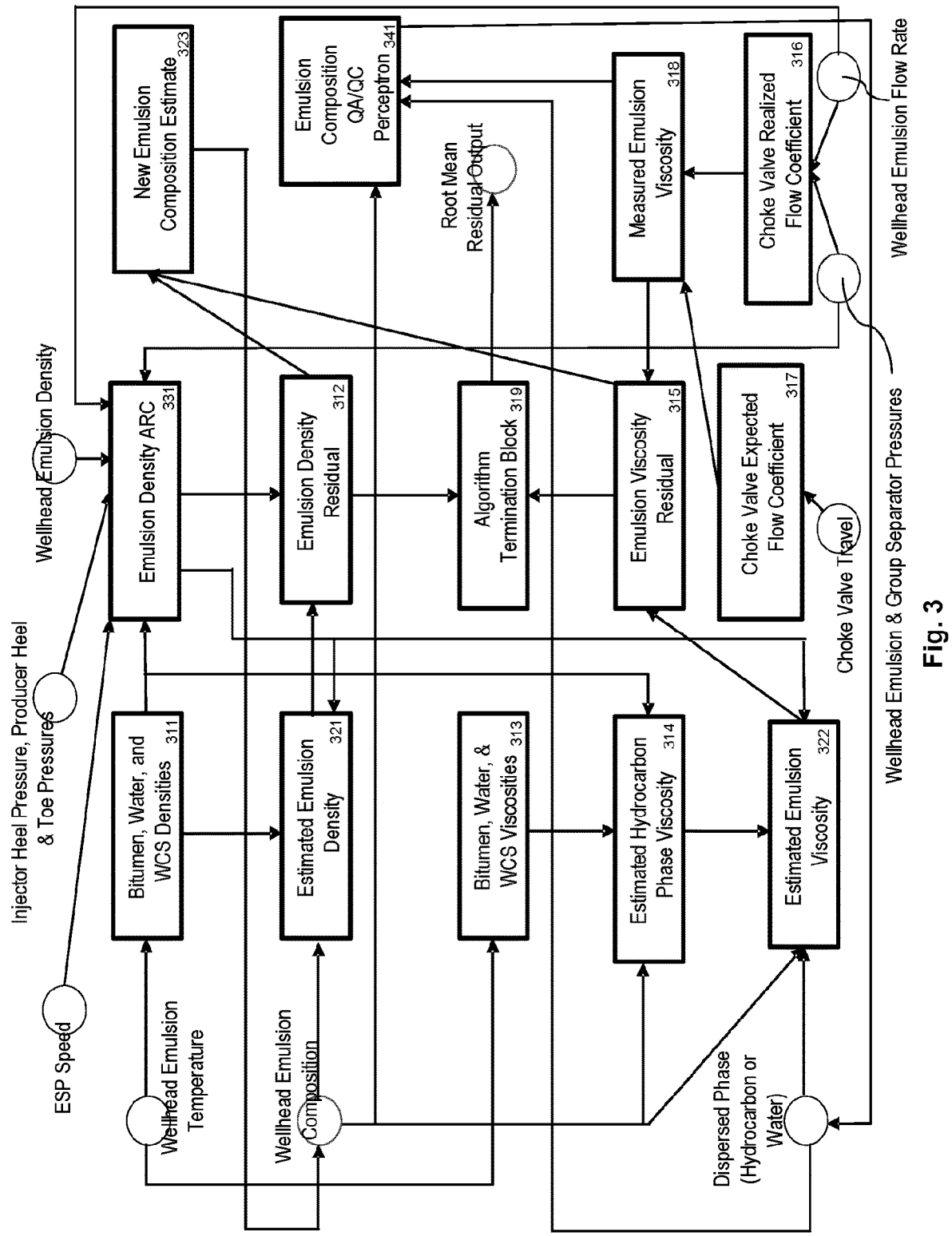
FIG. 3 is a flowchart illustrating aspects of an example method for sensing an estimated emulsion composition.
Figure 4:
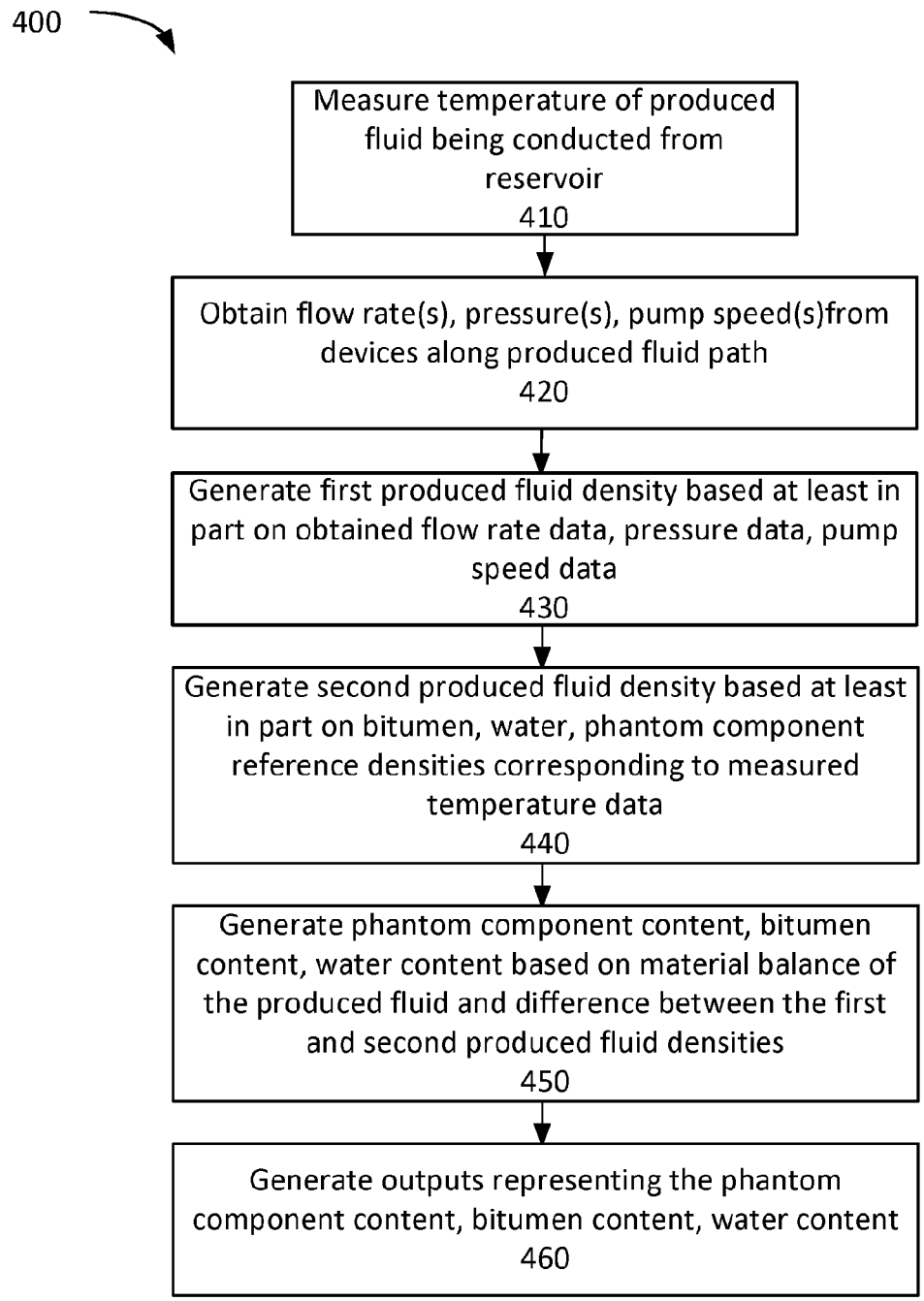
FIG. 4 is a flowchart illustrating aspects of an example method for sensing an estimated emulsion composition.
Figure 5:
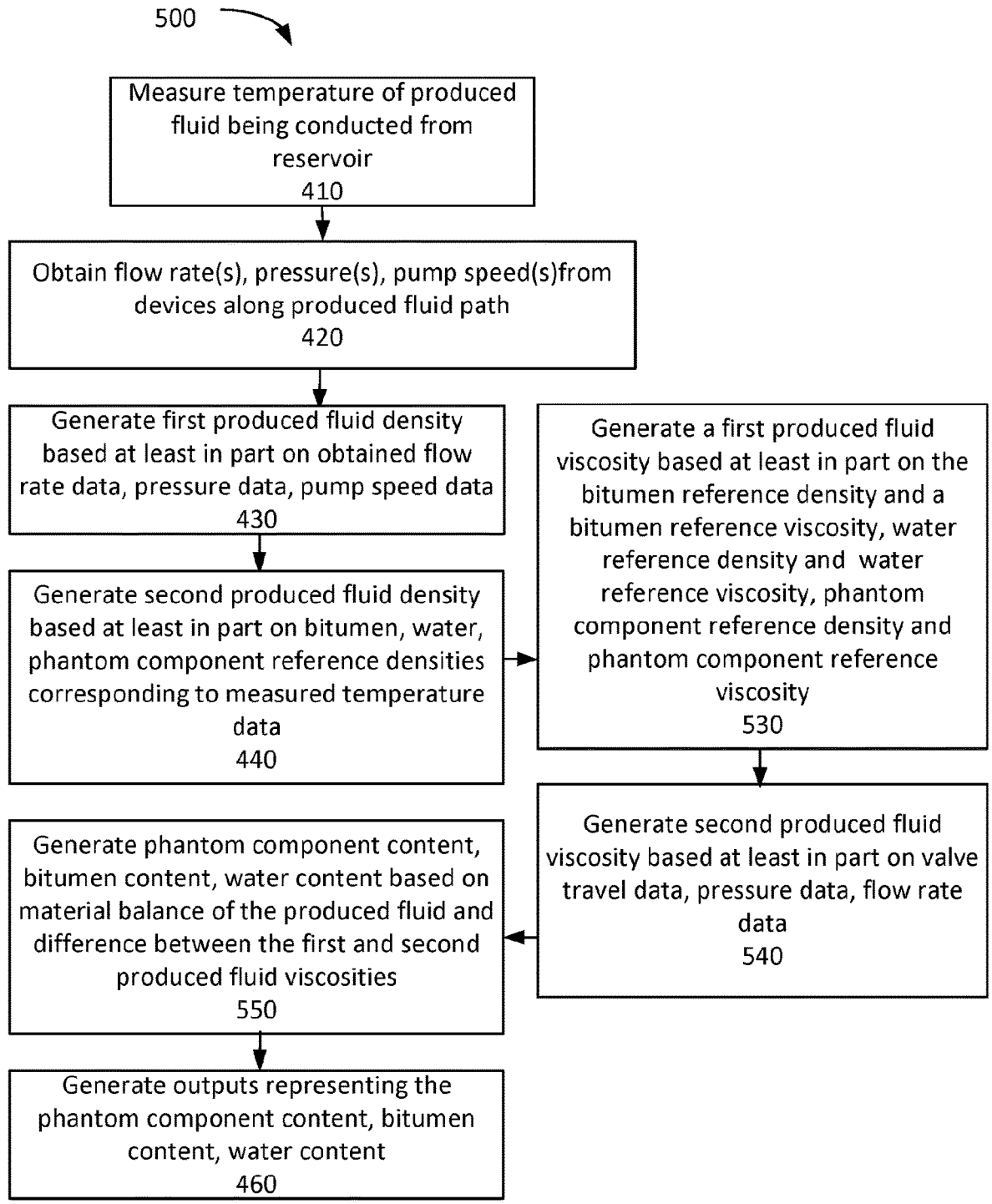
FIG. 5 is a flowchart illustrating aspects of an example method for sensing an estimated emulsion composition.

FIGS. 3, 4 and 5 show aspects of example processes for measuring an estimated produced fluid composition.

Broadly, in some embodiments, the process includes:
1. Reference water, bitumen, and WCS viscosities and densities are calculated at wellhead temperatures.

2. An Advanced Regulatory Control module is used to curate emulsion density using a secondary source of data and identify the presence of free gas or solids in the emulsion.
3. ARC's output is used to identify the emulsion as clean, contaminated with solids or contaminated with free gas. An educated guess about the emulsion composition is made based on previous sensor outputs.
4. Choke valve feed and discharge side pressures along with its stem travel are used to calculate emulsion viscosity. A classification based selector uses this viscosity along with other process variables to decide whether this emulsion viscosity has to be converted to emulsion's viscoelastic viscosity before being used in other parts of the network.
5. Emulsion composition QA/QC perceptron is called to configure the soft sensor to a setup that has the highest chance of calculating a valid emulsion composition, hence reducing the number of redundant calculations. This chance is estimated based on the soft sensor's previous runs.
6. Expected emulsion viscosity and density are calculated based on step 3's initial composition guess and emulsion contamination status.
7. Difference between expected and actual emulsion viscosities and differences are calculated.
8. A recursive algorithm (Gauss-Newton algorithm) is used to refine the composition guess until expected emulsion viscosities and densities calculated based on it become sufficiently close to their measured values.
9. Emulsion composition QA/QC perceptron evaluates the composition reported by step 8 and decides if the soft sensor has to be run with a different operating configuration to improve the composition estimate or if emulsion composition satisfies specific validity criteria or if a valid emulsion compositing cannot be estimated from the current dataset.

FIG. 4 shows aspects of an example method 400 for sensing an estimated composition of a produced fluid being conducted from the reservoir.

At 410, one or more sensors along the path of the produced fluid being conducted from the reservoir sense, measure or otherwise obtain one or more temperatures for the produced fluid. The temperature data from the sensors is transmitted to or is otherwise obtained by one or more devices for storage at one or more memory devices and/or for processing by density generator(s), viscosity generator(s) and/or composition generator(s).

At 420, flow rate data, pressure data, pump speed data and/or valve travel data is obtained from data from one or more input devices 130. As described herein or otherwise, in some embodiments, obtaining one or more of flow rate data, pressure data, and/or pump speed data can include processing, computing or otherwise transforming data sensed by one or more sensors into a form suitable for generating densities, viscosities and/or compositions. In some embodiments, this may include aspects of blocks 316 and 317 in FIG. 3. In some embodiments, pressure data includes pressures obtained from different locations including but not limited to well toe pressures, well heel pressures, heel injection pressures, wellhead produced fluid pressures, and the like. In some embodiments, pressure data includes data obtained from wellhead emulsion and separator pressures.

At 430, a first produced fluid density generator, processor and/or other computational device(s) generates a first density for the produced fluid being conducted from the reservoir. In some embodiments, the first density is based at least in part on the obtained flow rate data, pressure data, and pump speed data.

In some embodiments, generating the first density includes generating a backup produced density based at least in part on one or more of flow rate data, pressure data, and pump speed data.

In some embodiments, the first produced fluid density generator is configured to measure or otherwise obtain from at least one sensing device, a produced fluid density. As described herein or otherwise, the first produced fluid density generator can be configured to select either the measured density or the backup density as the first produced fluid density. In some embodiments, the measured density is selected when it falls within a density range between a water reference density based on the measured temperature of the produced fluid and a bitumen reference density based on the measured temperature of the produced fluid. In some embodiments, when the backup density is selected when the measured density is not within this range.

In some embodiments, the generation of the first density includes aspects of block 331 in FIG. 3.

In some embodiments, the first density generator is configured to generate a produced fluid contaminant indicator signal. This signal can provide an indication of whether the first density generator considers the produced fluid to be a clean emulsion, an emulsion contaminated with solids or a gas/liquid colloid emulsion.

At 440, a second produced fluid generator, processor and/or other computational device(s) generates a second density for the produced fluid being conducted from the reservoir. In some embodiments, generating the second density for the produced fluid (e.g. the emulsion) includes identifying the densities of bitumen, water and a phantom component at the measured temperature of the produced fluid. In some embodiments, the second produced fluid generator includes a neural network configured to generate the second density based on the densities of the bitumen, water and phantom component at the measured temperature.

In some embodiments, the neural network generates the second density based on the produced fluid contaminant indicator signal. In some embodiments, the produced fluid contaminant indicator signal is used to select or activate a neuron branch in the neural network.

In some embodiments, generating the second density for the produced fluid includes aspects of blocks 311 and 321 in FIG. 3.

At 450, a composition generator, processor and/or other computational device(s) generates a phantom component content, a bitumen content, and a water content based on the first and second densities for the produced fluid. In some embodiments, the composition generator includes an iterative convergence tool configured to adjust at least the phantom component content until a material balance of the produced fluid falls within a defined threshold or error range. In some embodiments, the iterative convergence tool is based on a material balance of the produced fluid, and a difference between the first density and the second density for the produced fluid.

In some embodiments, the generation of the composition components is based at least in part on the produced fluid contaminant indicator signal.

In some embodiments, generating the phantom component content, bitumen content and water content include aspects of blocks 312, 323, 319 and/or 341 in FIG. 3.

At 460, the composition generator, processor and/or other aspect of the system generates outputs representing the final phantom component content, bitumen content and water content after the iterative tool has completed its process. In some embodiments, the outputs are displayed on a screen or display panel. In some embodiments, the outputs are stored in one or more storage devices. In some embodiments, the outputs are transmitted to another device or system for monitoring.

In some embodiments, the outputs are monitored at the local device or remotely to trigger an alert if one or more aspects of the composition of the produced fluid being conducted from the reservoir violates one or more thresholds or changes at a rate that violates a threshold. In some instances, an alert can indicate a problem in one or more aspects of the system or an unexpected composition or change in composition for the produced fluid. In some instances, this may allow for changes to be made in the process with a smaller response time than waiting for lab results to determine a produced fluid composition.

For example, in some embodiments, the system can include an alert generator to monitor the outputs, and to trigger an alert when the water content meets a trigger condition. In some embodiments, the trigger condition is met when the water content is greater than or less than a defined threshold parameter. In some embodiments, the trigger condition is met when the water content changes by more than a defined threshold parameter. For example, in some instances, a large water content may be indicative that additional injection pressure may be required in the system. In some instances, a large change in water content or steam may be indicative of breakthrough. In some instance, the generated alert can provide an early warning of a problem or potential problem.

In some embodiments, the system may include a water cut sensor for measuring the water cut of the produced fluid being conducted from the reservoir. In some instance, these meters may have a large variance, may require calibration or recalibration, or may be prone to errors or failure. In some embodiments, the system includes a meter monitor configured to compare the output of the water cur sensor with the composition outputs (e.g. phantom component content, bitumen content, and/or water content) to determine whether there is a discrepancy. Upon detecting a discrepancy, the meter monitor can be configured to generate alert signals to identify a potential problem with the water cut sensor or to automatically recalibrate the water cut sensor. This may be similarly applied to any meter or sensor which produces similar outputs to the system described herein.

In some embodiments, the system may include an alert generator configured to generate an alert signal when the produced fluid contaminant indicator signal indicates that at least one of solids or gas is present the produced fluid. Solids and/or gas in the production line can be indicative of a problem in the production parameters and/or can cause damage to pumps and/or meters in the system. In some instances, the alert signal may provide an early warning to adjust production parameters, to shut down production processes, and/or to mitigate potential damage to components in the system.

FIG. 5 shows aspects of an example method 500 for sensing an estimated composition of a produced fluid being conducted from the reservoir. In some embodiments, similarly numbered aspects as described with respect to FIG. 4 are similar or identical to those in FIG. 5; however, in some embodiments, suitable variations may be used.

At 530, a first viscosity generator, processor and/or other computational device(s) generates a first viscosity for the produced fluid being conducted from the reservoir. In some embodiments, the first viscosity is based at least in part on: the reference density and the reference viscosity of bitumen at the measured temperature of the produced fluid, the reference density and the reference viscosity of water at the measured temperature of the produced fluid, and the reference density and the reference viscosity of the phantom component at the measured temperature of the produced fluid.

In some embodiments, generation of the first viscosity is based on a dispersed phase selection from multiple potential dispersed phases for the produced fluid.

In some embodiments, the first viscosity generator includes perception configured to create and maintain a dispersed phase selection matrix from previous selections by the perceptron. In some embodiments, the perceptron is configured to generate a dispersed phase selection based at least in part on the second produced fluid viscosity.

In some embodiments, generating the first viscosity includes aspects of blocks 313, 314 and 322 in FIG. 3.

At 540, a second viscosity generator, processor and/or other computational device(s) generates a second viscosity for the produced fluid being conducted from the reservoir. In some embodiments, the second viscosity is based at least in part on the valve travel data, pressure data and flow rate data.

In some embodiments, the second viscosity generator includes a neural network configured to generate the first viscosity based on the densities and viscosities of the bitumen, water and phantom component at the measured temperature. In some embodiments, the neural network generates the second viscosity based on the produced fluid contaminant indicator signal. In some embodiments, the produced fluid contaminant indicator signal is used to select or activate a neuron branch in the neural network.

In some embodiments, generating the second viscosity includes aspects of blocks 316, 317 and 318 in FIG. 3

At 550, a composition generator, processor and/or other computational device(s) generates a phantom component content, a bitumen content, and a water content based on the first and second densities for the produced fluid. In some embodiments, the composition generator includes an iterative convergence tool configured to adjust at least the phantom component content until a material balance of the produced fluid falls within a defined threshold or error range. In some embodiments, the iterative convergence tool is based on a material balance of the produced fluid, and a difference between the first density and the second density for the produced fluid, and/or a difference between the first viscosity and the second viscosity for the produced fluid.

In some embodiments, the generation of the composition components is based at least in part on the produced fluid contaminant indicator signal.

In some embodiments, generating the phantom component content, bitumen content and water content include aspects of blocks 312, 315, 323, 319 and/or 341 in FIG. 3.

FIG. 3 shows aspects of an example method 300 for sensing an estimated composition of a produced fluid being conducted from the reservoir. In some embodiments, the system comprises a soft sensor for sensing or otherwise estimating a produced fluid composition. In some embodiments, the system can identify the presence of significant amounts of solids and/or free gas in the produced fluid.

In some instances, the systems and methods described herein may be utilized or applied in for SAGD produced fluids such as a SAGD wellhead emulsion. In some instances, the systems and methods described herein may utilize or may otherwise be applied to existing wells and instrumentation. Accordingly, in some instances, this may reduce or eliminate the need to install or rely on additional or specialized instrumentation to detect a wellhead produced fluid composition and/or to identify the presence of amounts of solids and/or free gas in the produced fluid.

In some embodiments, the system measures, detects, calculates or otherwise receives data streams including emulsion wellhead density, temperature and flow rate; ESP speed; producer heel and toe pressures; injector heel pressure; wellhead emulsion choke valve stem travel; and emulsion pressure after the emulsion choke valve (e.g. wellpad group separator pressure or emulsion header pressure).

In some embodiments, the system is configured to sense or otherwise estimate the composition of the produced fluid. In some examples, the produced fluid can be the liquid portion of an emulsion which may be treated as consisting of water, bitumen and a phantom component. In some instances, the phantom component can capture or otherwise compensate for the long-term lightening of bitumen over time and/or can reduce or prevent the system's parameters and outputs from drifting based on the long term lightening of bitumen over time.

In some embodiments, the Western Canadian Select crude oil (WCS) can be used as the phantom component. However, in other embodiments, other phantom components may be used. In some examples, the phantom component may be based on a well location or reservoir characteristics. Based on the drift of the bitumen, in some instances, the phantom component should be lighter and/or less viscous than bitumen.

In some embodiments, the phantom component may be immiscible in water and miscible in bitumen. In some instances, the produced fluid composition can be generated as an combination of water and a phantom component/reference bitumen blend (reflecting the production bitumen) with the blend's phantom component being calculated by the system as described herein.

In some embodiments, the system can sense the wellhead emulsion in terms of emulsion reference bitumen, water, phantom component (e.g. Western Canadian Select), solids, free gas contents. In some instances, the sum of WCS and reference bitumen contents reflect the emulsion's total bitumen content. Separate reporting may be done to obtain a measure of bitumen's lightening over time.

In some embodiments, to minimize the impact of input data error and instrumentation systems' deviations on predicted values, the system's artificial neural networks are combined with the Gauss-Newton optimization algorithm to minimize the overall difference between observed emulsion density and viscosity with their counterparts calculated by the system. In some instances, the system outputs the result of this optimization exercise by reporting the average mean root of the relative difference between emulsion's measured density and viscosity with those calculated from the soft sensor based on its reported emulsion composition. In some instances, this output can be used for continuous quality assurance/quality control of the system outputs.

In some embodiments, a permissive can be installed on this soft sensor that turns it off if ESP speed drop bellows 5 Hz which can be indicative of either an upset or a shut-in. This is done since some parts of this soft sensor are utilizing prior-learning optimization modules. These modules rely on fixed size databases that the soft sensor is continuously filling by overwriting oldest entries with newer ones. By reducing or eliminating data from shut-ins and upsets, the system may prevent iterative or learning components or databases from including unrepresentative and noisy data.

In some embodiments, the system includes a deep neural network which can include machine learning subroutines that utilize convolutional neural networks, advanced regulatory controls (ARCs) and perceptrons.

At 311, the system generates reference densities for bitumen, water and phantom component models based on the measured temperature of the produced fluid. In some embodiments, these models are stored, created, or otherwise implemented based on simulations, formulas, models, regression analysis and/or bitumen composition assay information.

In some examples, generating a model or correlation between bitumen density and temperature data can be done using an ASPEN HYSYS™ petroleum assay tool and bitumen composition assay information.

Equation 1 can provides an acceptable correlation between hydrocarbons' temperature and density. As such, it can be used as a basis to develop a similar correlation for bitumen.

$$\rho = \phi_0 \phi_1^{-\left(1-\frac{T}{T_C}\right)^{\phi_2}} \tag{1}$$

The critical temperature of bitumen is not known. Thus, it is another variable that has to be estimated through regression analysis and is replaced by $\phi_3$ to generate equation 2. This equation cannot be used in a linear regression model to estimate its coefficients due to its non-linear nature. As such, it is linearized through manipulations outlined in equations 2 to 4.

$$\rho = \phi_0 \phi_1^{-\left(1-\frac{T}{\phi_3}\right)^{\phi_2}} \xrightarrow{\text{Natural lof of both sides}} \tag{2}$$

$$\ln \rho = \ln \phi_0 - \left(1 - \frac{T}{\phi_3}\right)^{\phi_2} \ln \phi_1 \rightarrow \tag{3}$$

$$\ln \rho = \ln \phi_0 + \left(1 - \frac{T}{\phi_3}\right)^{\phi_2} \ln \phi_1^{-1} \tag{4}$$

Figure 6:
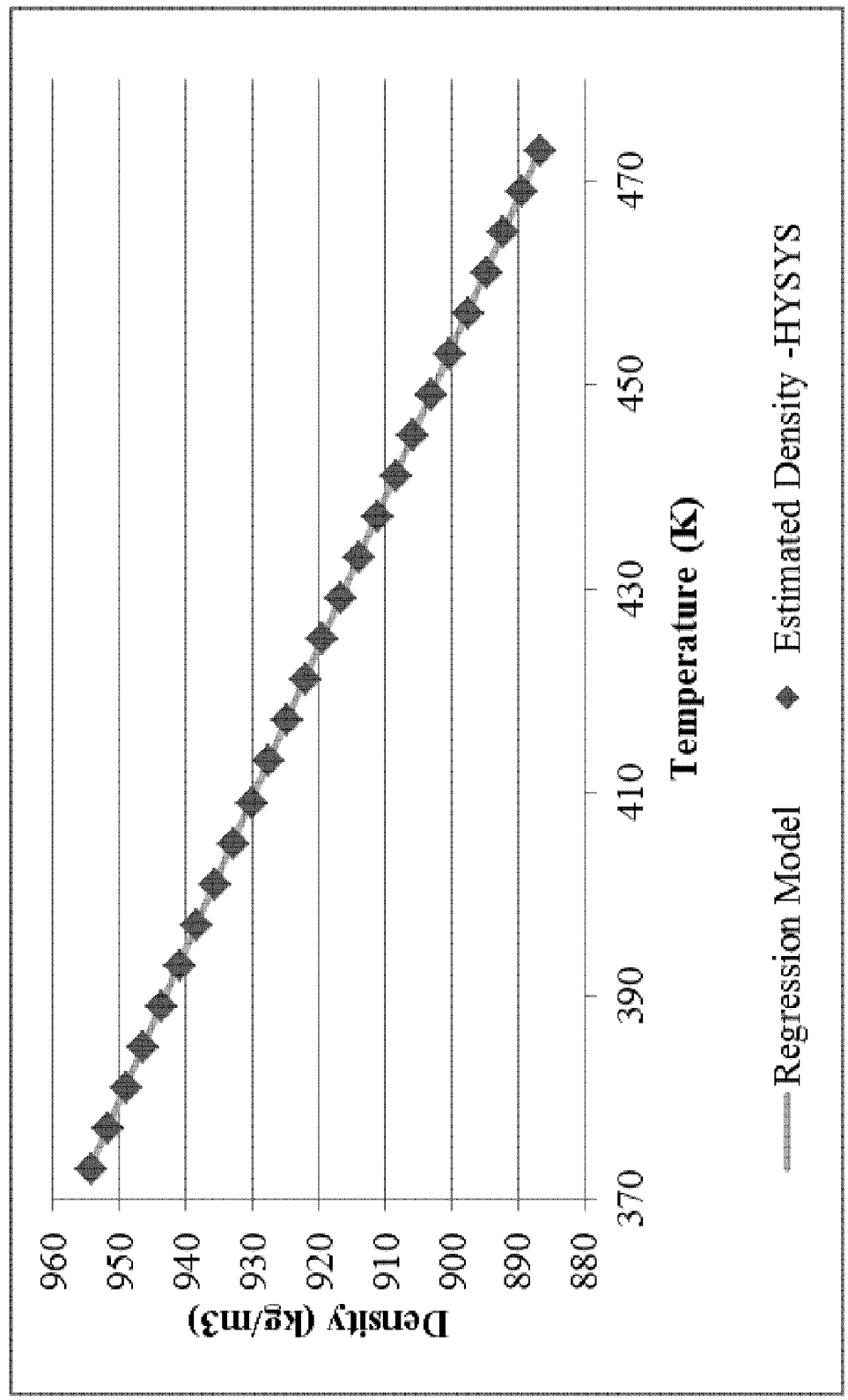
FIG. 6 is an example line graph showing bitumen density vs. temperature.

Equation 4 is not explicit in terms of either density or temperature. As such, it still cannot be readily used in linear regression models. Further linearization of equation 4 is possible through, for example, Taylor Series expansion or using natural logarithms. However, doing so may reduce the accuracy of the developed model or may even create mathematically insoluble solutions. As such, equation 7's coefficients are estimated using a combination of optimization and regression problems. In other words, $\phi_0$ and $\phi_1$ are estimated using linear regression model while $\phi_2$ and $\phi_3$ are estimated via optimization techniques with a goal of maximizing $R^2$ of fitting of equation 4 into the data. Results of this fit-optimization are shown in equation 5 and FIG. 6.

$$\rho = 308.7 \times 0.2577^{-\left(1-\frac{T}{1022}\right)^{0.4034}} \quad R^2 = 0.999 \tag{5}$$

Emulsion water reference density is calculated using equation 6 that has been developed by AIChE's DIPPR.

$$\rho_{water} = \frac{0.14395}{0.01121^{1+\left(1-\frac{T}{649.7}\right)^{0.05107}}} \tag{6}$$

Figure 7:
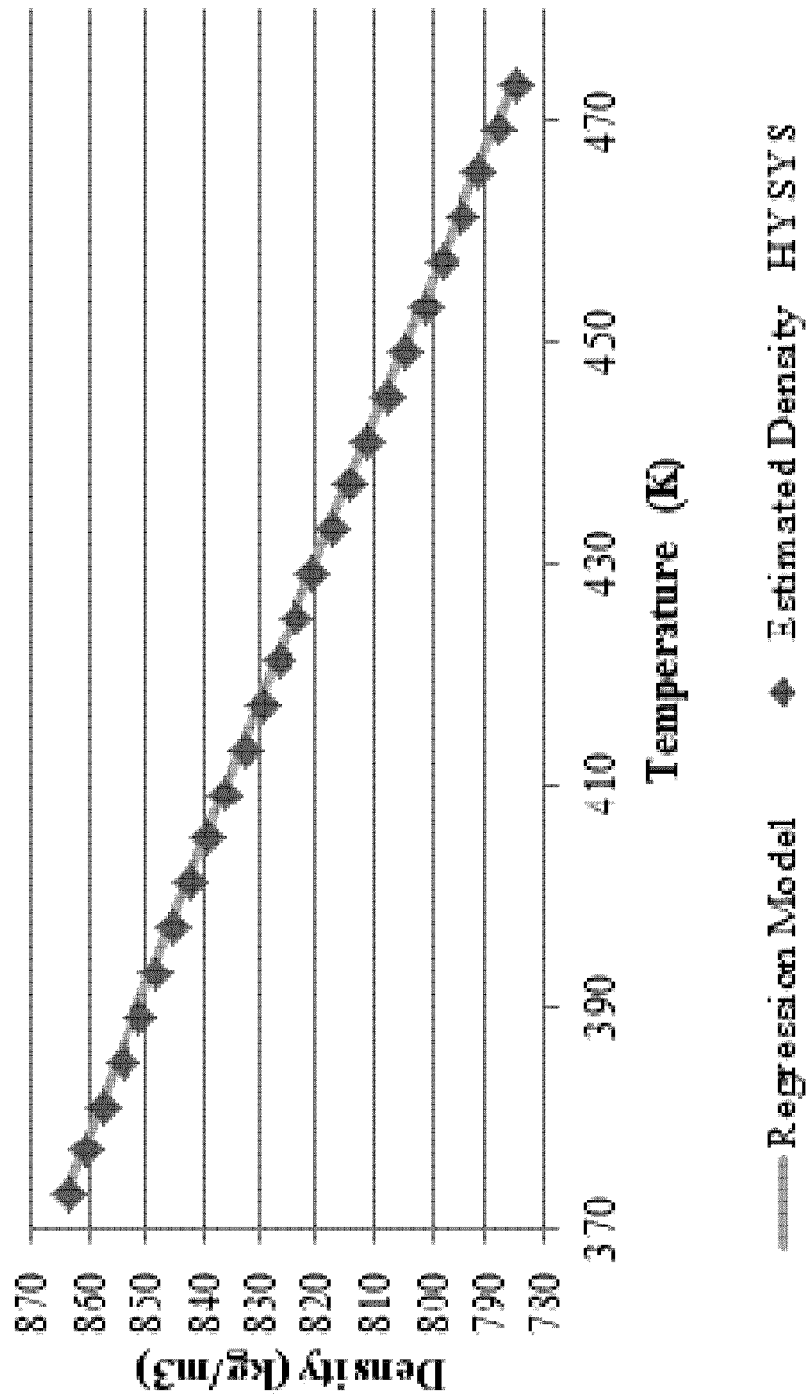
FIG. 7 is an example line graph showing Western Canadian Select crude oil density vs. temperature.

The same approach employed to estimate reference bitumen density may be utilized to estimate reference phantom component (e.g. WCS) density. In some embodiments, this is based on a petroleum assay which is used to create the HYSYS model. Example, resultant density-temperature correlation and associated graph are summarized in equation 7 and FIG. 7.

$$\rho = 349.2 \times 0.3132^{-\left(1-\frac{T}{750.2}\right)^{0.3611}} \quad R^2 = 0.999 \quad (7)$$

At 312, the system can use Equation 8 to calculate emulsion density residual. This residual outlines the difference between emulsion density calculated from the soft sensor's estimated emulsion composition and the measured density.

$$r_1(X_j) = \rho_{emulsion\ calculated}(X_j) - \rho_{emulsion\ measured} \quad (8)$$

At 313, the system generates reference viscosities for bitumen, water and phantom component models based on the measured temperature of the produced fluid. In some embodiments, these models are stored, created, or otherwise implemented based on simulations, formulas, models, regression analysis and/or bitumen composition assay information.

Figure 8:
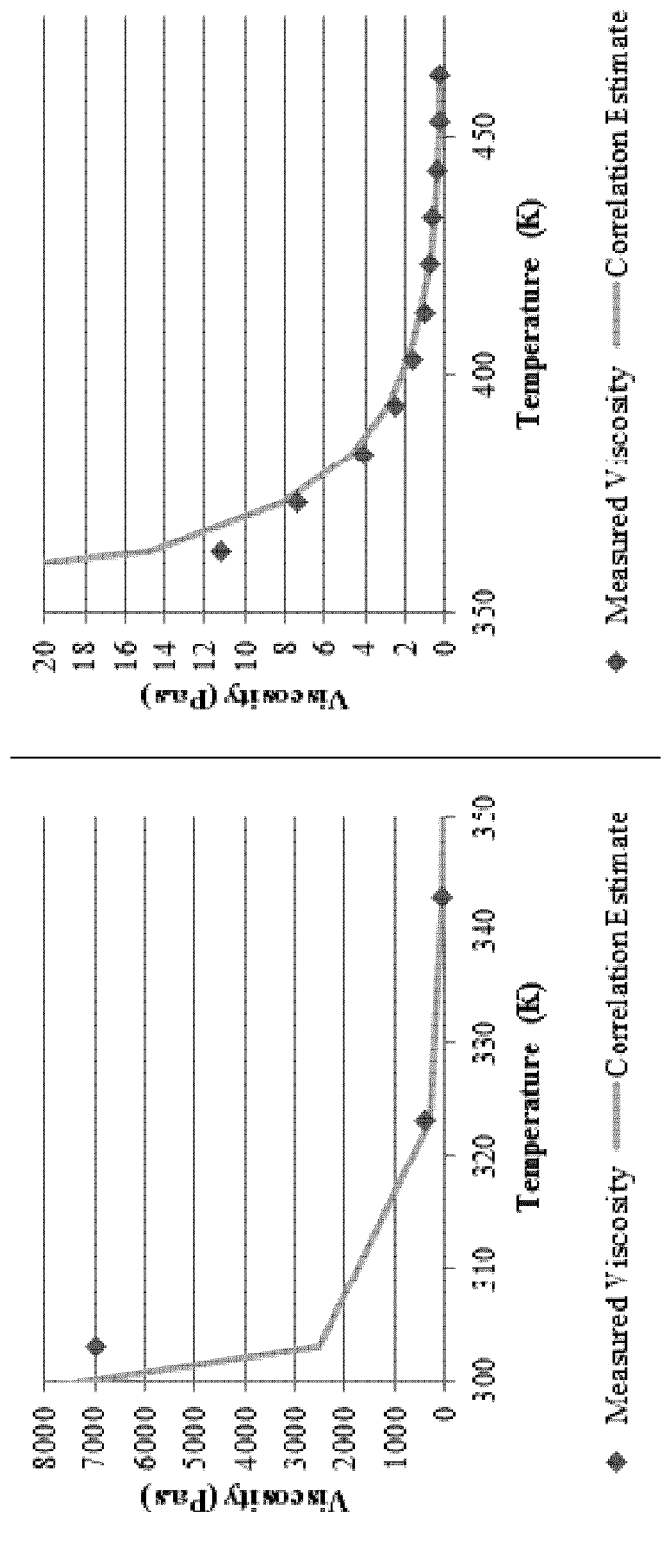
FIG. 8 shows example line graphs of bitumen viscosity vs. temperature.

An example bitumen viscosity at varying temperatures has been measured through laboratory analysis. Equation 9 is fitted into this data to generate a correlation between process temperature and pure bitumen viscosity. Results of this fit are summarized in equation 10 and FIG. 8.

$$\ln[\ln(\mu)] = \kappa_0 + \kappa_1 \ln T \quad (9)$$

$$\ln[\ln(\mu_B)] = 16.23 - 2.369 \ln T \quad R^2 = 0.994 \quad (10)$$

In some embodiments, water viscosity is calculated using equation 11.

$$\mu_W = 2.414 \times 10^{-5} \times 10^{\left(\frac{247.8}{T-140}\right)} \quad (11)$$

Figure 9:
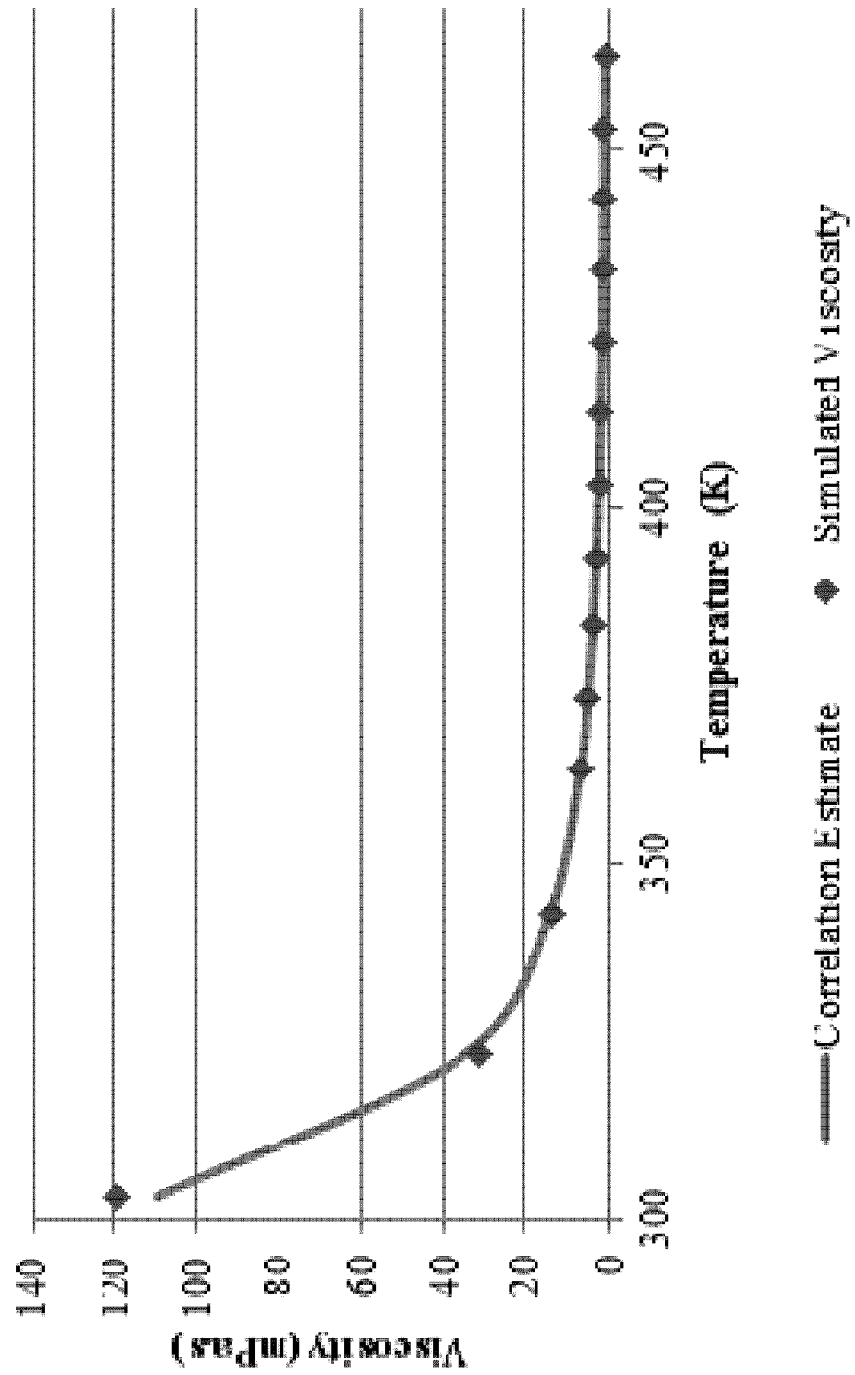
FIG. 9 is an example line graph showing Western Canadian Select crude oil viscosity vs. temperature.

Similar to the viscosity of bitumen at various temperatures, the phantom component can be similarly tested to generate a model for the viscosity of the phantom component at various temperatures. In some embodiments, the phantom component is WCS. In one example sample, WCS viscosities were estimated using ASPEN HYSYS™ and the petroleum assay generated for WCS. In some instances, HYSYS is able to produce relatively accurate viscosity estimates if heavy oil's residue and bulk viscosities are provided to it. Similar to bitumen viscosity correlation development outlined in with respect to block 313, equation 9 is fitted into viscosity vs. temperature data to generate equation 12 and FIG. 9.

$$\ln[\ln(10 \times \mu_{WCS})] = 17.953 - 2.801 \ln T \quad R^2 = 0.994 \quad (12)$$

At 314, the system determines a hydrocarbon phase viscosity. In some situations, emulsions can be considered to consist of two distinct phases: water phase and hydrocarbon phase. Therefore, the relation between emulsion composition and viscosity should account for interactions both between and within phases. This may be done by first establishing a relationship between hydrocarbon phase's viscosity and emulsion composition (block 314) and then using this relation in development of a link between overall emulsion viscosity and emulsion composition (block 322).

In some embodiments, the hydrocarbon phase is comprised of bitumen and WCS. Since both of these compounds are hydrocarbons and miscible in each other, the Refutas hydrocarbon blend viscosity calculation method is used to establish a relationship between hydrocarbon phase's viscosity and emulsion composition. In some embodiments, this method includes:

1. Bitumen and WCS viscosities at process temperature are calculated (block 313).
2. Bitumen and WCS densities at process temperature are calculated (block 311).
3. Bitumen and WCS kinematic viscosities at process temperature are calculated using equation 13.

$$v = \mu \rho^{-1} \quad (13)$$

4. Bitumen and WCS blending numbers are calculated using equation 14.

$$VBN = 14.53 \times \ln[\ln(v[cSt] + 0.8)] + 10.98 \quad (14)$$

5. Hydrocarbon phase's total blending number is calculated using equation 15.

$$VBN_{HC} = \frac{x_B}{x_B + x_{WCS}} VBN_B + \frac{x_{WCS}}{X_B + x_{WCS}} VBN_{WCS} \quad (15)$$

6. Hydrocarbon phase's kinematic viscosity is calculated using equation 16.

$$v_{HC}[cSt] = \exp\left(\exp\left(\frac{VBN_{HC} - 10.98}{14.53}\right)\right) - 0.8 \quad (16)$$

7. Hydrocarbon phase's density is calculated using equation 17.

$$\rho_{HC} = \left(\frac{x_B}{\rho_B(x_B + x_{WCS})} + \frac{x_{WCS}}{\rho_{WCS}(x_B + x_{WCS})}\right)^{-1} \quad (17)$$

8. Hydrocarbon phase's dynamic viscosity is calculated using equation 18.
(18)

$$\mu_{HC} = v_{HC} \rho_{HC} \quad (18)$$

At 315, equation 19 is used to calculated emulsion viscosity residual. This residual outlines the difference between emulsion viscosity calculated from the current estimated emulsion composition and the measured viscosity.

$$r_2(X_j) = \mu_{emulsion\ calculated}(X_j) - \mu_{emulsion\ measured} \quad (19)$$

A valve flow coefficient (block 316) is a measure of a valve's efficiency at countenancing fluid flow and is defined in imperial units as outlined in equation 20. For calculation purposes, valve feed port pressure may be assumed to be equal to wellhead emulsion pressure and valve discharge port pressure may be assumed to be equal to that of the wellpad emulsion header. Emulsion flow and specific gravity are obtained from wellhead coriolis meter readings.

$$C_v = F\ [USGPM] \sqrt{\frac{SG}{\Delta P\ [PSI]}} \quad (20)$$

Figure 10:
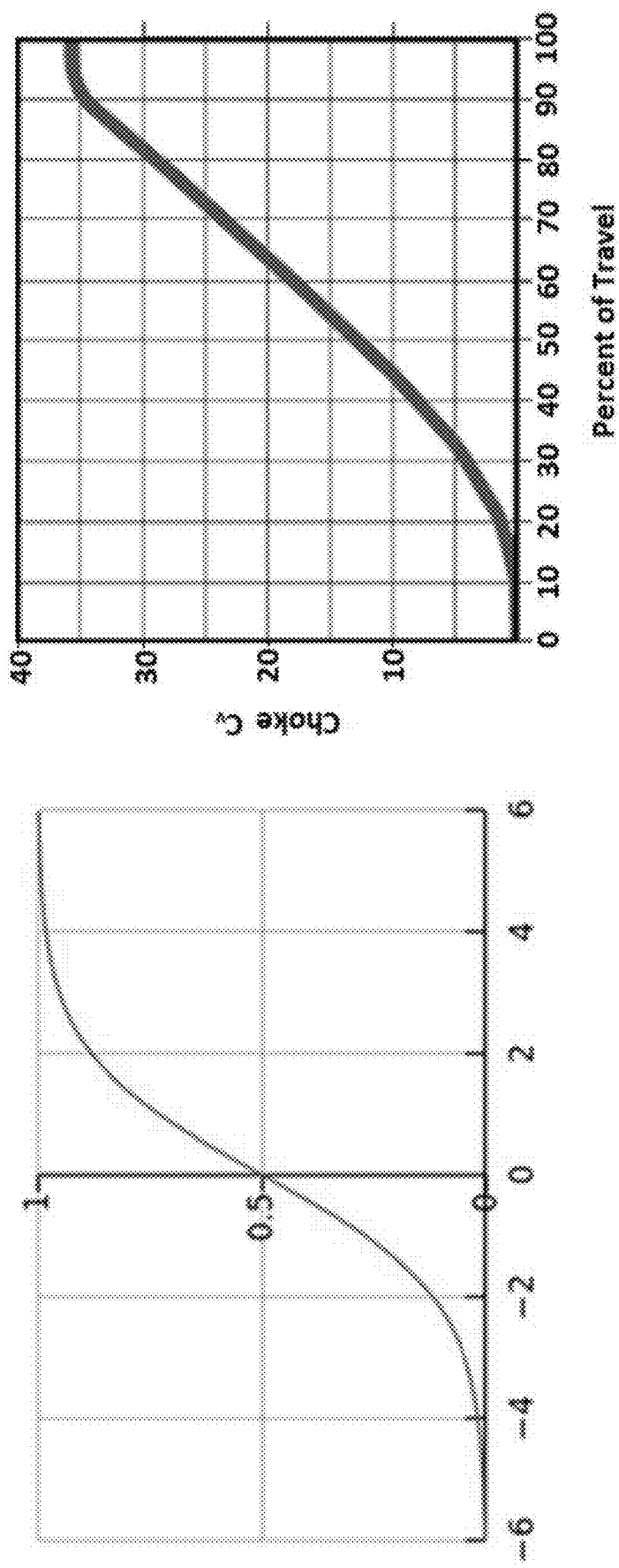
FIG. 10 shows line graphs of an example logistic curve and a choke valve flow characteristic curve.

A typical choke valve characteristic curve outlining the relation between valve flow coefficient and stem travel is shown in FIG. 10. As this figure shows, shape of choke valve characteristic curve is similar to that of a logistic function. Hence, the system determines the expected flow coefficient of the valve in two steps (block 316). First, a logistic equation, outlined in equation 21, is fitted into the choke valve's datasheet flow coefficient vs. stem travel information as described below. Then, the valve's expected flow coefficient at any moment is calculated by plugging the valve's stem travel recorded by DCS into the valve's $C_v$ logistic function.

$$C_v(\text{Expected}) = \frac{A_o}{1 + \exp(-A_1[\text{Travel} + A_2])} \quad (21)$$

Equation 21 can be linearized to simplify the process of fitting it into choke valve datasheet information. This is done by first inversing both sides of equation 21 to generate equation 22. This equation is then modified into equation 23. Finally, the natural logarithm of both sides of equation 23 is taken to generate equation 24.

$$C_V^{-1}(\text{Expected}) = A_o^{-1} + A_o^{-1} \exp(-A_1[\text{Travel} + A_2]) \quad (22)$$

$$C_V^{-1}(\text{Expected}) - A_o^{-1} = A_o^{-1} \exp(-A_1[\text{Travel} + A_2]) \quad (23)$$

$$\ln(C_V^{-1}(\text{Expected}) - A_o^{-1}) = \ln A_o^{-1} - A_1 \text{Travel} - A_1 A_2 \quad (24)$$

Equation 24 is not explicit in terms of either valve travel or expected flow coefficient. As such, it cannot still be readily used in linear regression models. Thus, equation 24's coefficients are estimated using a combination of optimization and regression problems. In other words, $A_2$ and $A_1$ are estimated using a linear regression model while $A_o$ is estimated via optimization techniques with a goal of maximizing the linear regression model's $R^2$. Assuming that Microsoft Excel™ is used to perform this optimization-linear regression operation, the produced function will have a setup similar to equation 25 with Excel explicitly reporting $A_o$ as the output of its solver function. Hence, $A_1$ and $A_2$ are estimated as outlined in equations 26 and 27 respectively.

$$\ln(y) = B_o + B_1 x \quad (25)$$

$$A_1 = -B_1 \quad (26)$$

$$A_2 = \frac{B_o - \ln A_o^{-1}}{-A_1} \quad (27)$$

Figure 11:
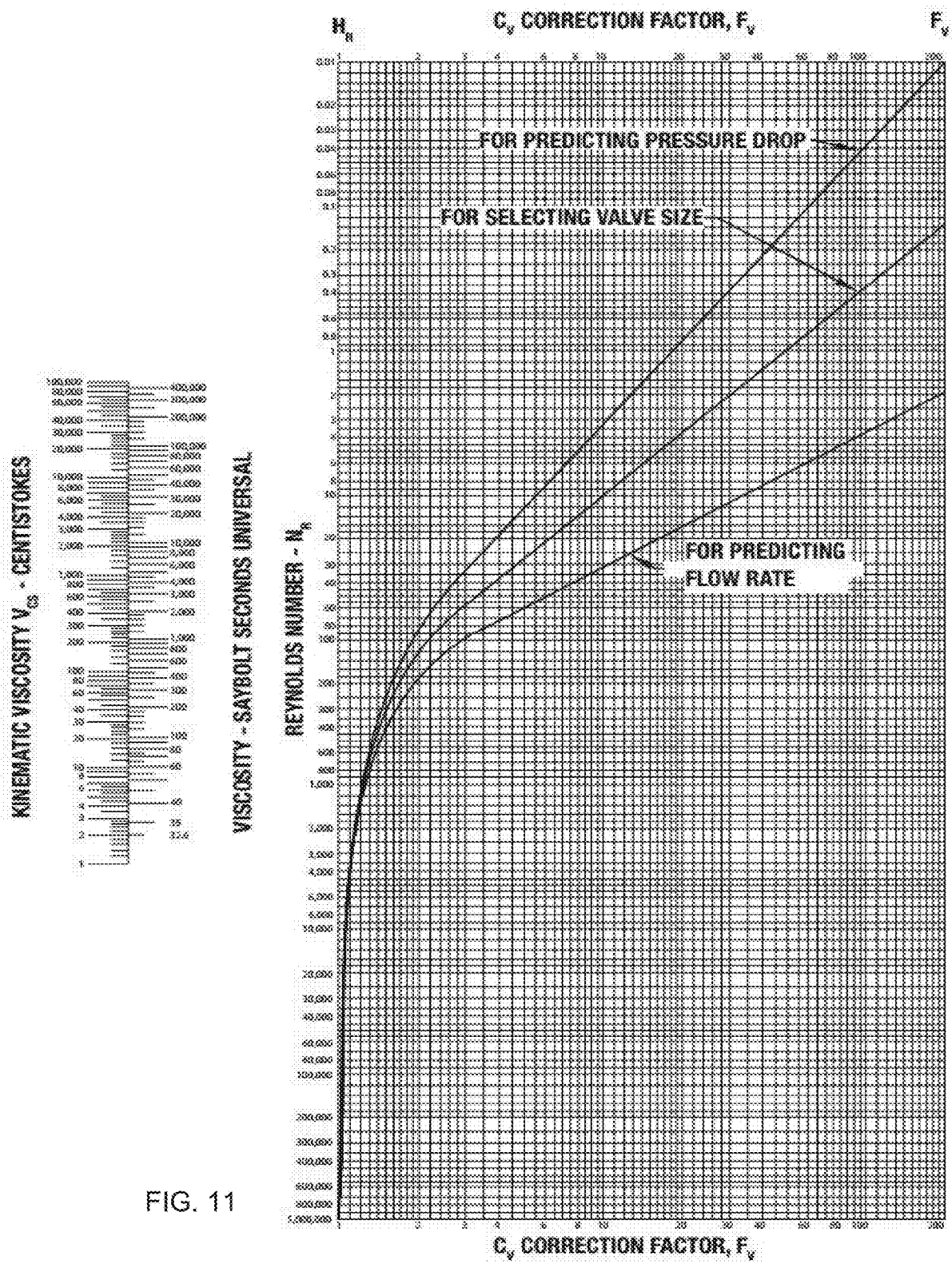
FIG. 11 is a nomograph outlining the impact of viscosity on valve flow coefficient correction factor.

Valves' published flow coefficients are generally determined using water as the flow medium. Hence the effect of viscosity on flow coefficients is not reflected in them. This neglected viscosity effect is quantified by defining a flow coefficient correction factor as outlined in equation 28. The relationship between this factor and flow's valve Reynolds number (shown in FIG. 11) is exploited to estimate the flow's viscosity since flow's valve Reynolds number has an inverse relationship with the valve's viscosity as shown in equation 29.

$$F_V = \frac{C_v(\text{Realized})}{C_v(\text{Expected})} \quad (28)$$

$$N_R = \frac{1.725 \times 10^{-5} \times Q[USGPM] \rho}{\sqrt{C_v(\text{Expected})} \, \mu} \quad (29)$$

In some embodiments, based on the above, the system generates the produced fluid viscosity. First, the valve flow coefficient correction factor is calculated using equation 28. This correction factor is then substituted into equation 30, which has been obtained from FIG. 11, to estimate the fluid's valve Reynolds number. Finally, this estimated Reynolds number is substituted in equation 31, which is a re-arrangement of equation 29, to estimate emulsion's viscosity.

$$N_R = \exp(-1.761 \ln(\ln F_v) + 4.126) \quad 1 \leq F_v \leq 2.2 \quad R^2 = 0.991 \quad (30)$$

$$\mu = \frac{1.725 \times 10^{-5} \times Q[USGPM] \rho}{\sqrt{C_v(\text{Expected})} \, N_R} \quad (31)$$

In some instances, the presence of flow coefficient correction factors smaller than one causes equation 30 to be insolvable in the real numbers domain. Choke valve's expected flow coefficient being smaller than its realized value leads to equation 32 which is based on equation 30. This equation does not have a solution in the domain of real numbers. However, equation 32 can be written into equation 33 via expansion of the model's numerical domain from real to complex numbers and application of the Complex Logarithmic Number principle. Re-arranging this equation to separate its complex and real parts leads to equation 34 and application of Euler's formula to equation 34 leads to equation 35; this equation provides a complex estimate of the choke valve's Reynolds number in situations in which the flow coefficient correction factor is less than one.

$$N_R = \exp(-1.761 \ln(-|\ln F_v|) + 4.126) \quad (32)$$

$$N_R = \exp(-1.761 [\ln(|\ln F_v|) + i\pi] + 4.126) \quad (33)$$

$$N_R = e^{-1.761 \ln(|\ln F_v|)+4.126} e^{-1.761 i\pi} \xrightarrow{e^{-1.761 \ln(|\ln F_v|)+4.126} = \psi} \quad (34)$$

$$N_R = \psi \cos(-1.761\pi) + i\psi \sin(-1.761\pi) \quad (35)$$

As discussed above, emulsion viscosity is calculated by substituting choke valve's Reynolds number into equation 31. Doing so in this situation, i.e. substituting equation 35 into equation 31, leads to equation 36. Manipulations outlines in equations 36 to 39 turn equation 36 into equation 40.

$$\mu = \frac{1.725 \times 10^{-5} \times Q[USGPM] \rho}{\sqrt{C_v(\text{Expected})} \, (\psi \cos(-1.761\pi) + i\psi \sin(-1.761\pi))} \quad (36)$$

$$\mu = \frac{\frac{1.725 \times 10^{-5} \times Q[USGPM] \rho}{\sqrt{C_v(\text{Expected})}}}{(\psi \cos(-1.761\pi) + i\psi \sin(-1.761\pi))} \xrightarrow{\varsigma} \times \frac{(\psi \cos(-1.761\pi) - i\psi \sin(-1.761\pi))}{(\psi \cos(-1.761\pi) - i\psi \sin(-1.761\pi))} \quad (37)$$

$$\mu = \frac{\varsigma(\psi \cos(-1.761\pi) - i\psi \sin(-1.761\pi))}{(\psi^2 \cos^2(-1.761\pi) + \psi^2 \sin^2(-1.761\pi))} \xrightarrow{\sin^2 x + \cos^2 x = 1} \quad (38)$$

-continued $$\mu = \frac{\varsigma(\psi\cos(-1.761\pi) - i\psi\sin(-1.761\pi))}{\psi^2} \qquad (39)$$

$$\mu = \frac{\varsigma\cos(-1.761\pi)}{\psi} - \frac{\varsigma\sin(-1.761\pi)}{\psi}i \qquad (40)$$

The viscosity function shown in equation 40 refers to a specific type of viscosity known as the complex viscosity. In general, the real part of this equation is equal to the mixture's dynamic viscosity and the imaginary part of it is a measure of the mixture's elasticity. Hence, emulsion's dynamic viscosity in situations in which the choke valve's flow coefficient correction factor is less than one is calculated using equations 41 to 43.

$$\mu = \frac{\varsigma\cos(-1.761\pi)}{\psi} \qquad (41)$$

$$\varsigma = \frac{1.725 \times 10^{-5} \times Q[USGPM]\rho}{\sqrt{C_v(\text{Expected})}} \qquad (42)$$

$$\psi = e^{-1.761\ln(|\ln F_v|)+4.126} \qquad (43)$$

In some embodiments, the system attempts to minimize the overall residual of its core functions. Performance may be monitored by estimating the root mean square of emulsion viscosity and density residuals as outlined in equation 44. As such, output of this computation is used for model quality assurance. This residual is also used as a basis for the algorithm termination block 319. In some embodiments, the soft sensor's emulsion composition estimation algorithm is terminated and the latest iteration's emulsion composition estimate is deemed to be the final one if number of iterations exceeds a defined number (e.g. 1000) or $R(X_{j+1})$ drops to below a defined threshold (e.g 0.02). In some embodiments, the system only terminates the composition estimation iteration tool and not the larger neural network which is controlled by the QA/QC Perceptron at 341. In the termination block, the system identifies a emulsion composition estimate that provides a reasonable solution to the composition estimation process and activates the perceptron. In some embodiments, the perceptron is configured to evaluate the estimated composition and if it deems the estimate a valid value, it will terminate the whole neural network process. Otherwise, it may adjusts neural network's configuration and restart the composition estimation process.

$$r_t(X_{j+1}) = \sqrt{0.5\frac{r_1^2(X_{j+1})}{\rho_{\text{emulsion measured}}^2} + 0.5\frac{r_2^2(X_{j+1})}{\mu_{\text{emulsion measured}}^2}} \qquad (44)$$

At 321, the system generates a produced fluid density. In some embodiments, the system aspects for generating the produced fluid density at 321 include a neural network such as a convolutional neural network. In some embodiments, the neural network is trained to perform overlapping density estimation analyses.

Figure 12:
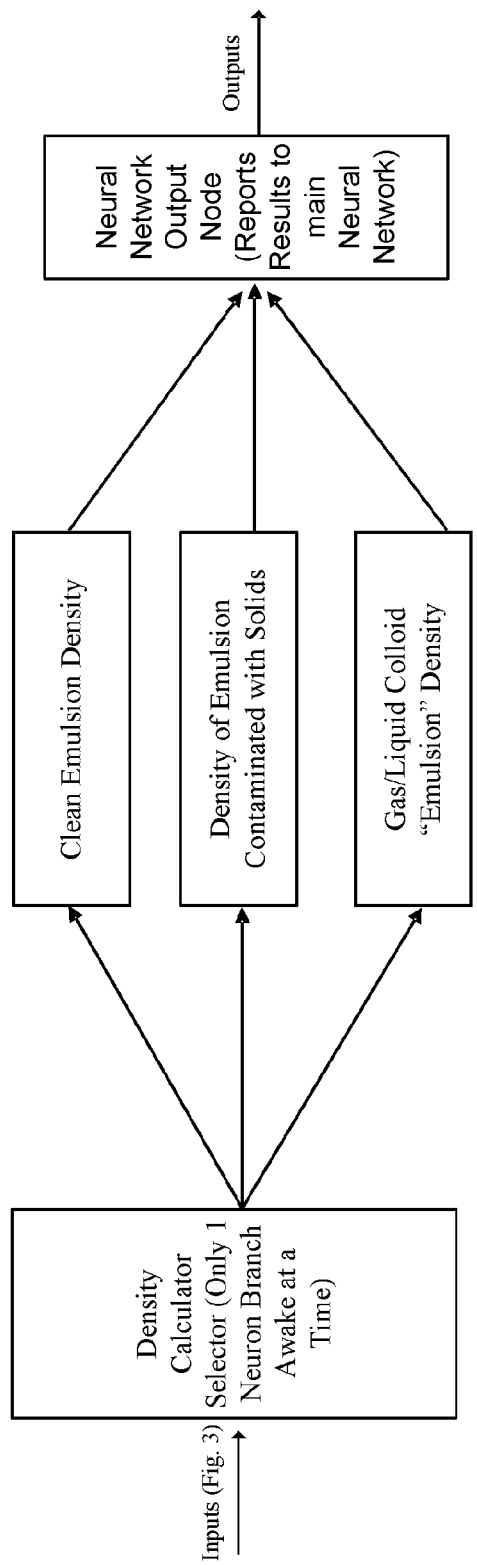
FIG. 12 is a flowchart illustrating aspects of an example neural network for generating produced fluid density.

In some embodiments, in an effort to achieve a faster convergence, the neural network includes a selector that receives a produced fluid contaminant (e.g. gas/solid/no-contaminant) signal from the emulsion density ARC and only awakens the neuron(s) corresponding to the ARC signal. In some embodiments, three neurons/neuron sets/branches embedded in the neural network each determine the density of a clean emulsion (i.e. an emulsion with no free gas or solids), an emulsion contaminated with free gas, and an emulsion contaminated with solids using the emulsion composition node's data and reference densities. FIG. 12 shows aspects of an example neural network including the three neural network branches which may be selected by the produced fluid contaminant signal.

For a clean emulsion density, the relation between emulsion density and composition in absence of free gas and solids is outlined in equation 45. In some embodiments, emulsion density is generated in block 331, and reference bitumen, water and phantom component (e.g. WCS) densities are generated in block 311.

$$\rho_{\text{emulsion}}^{-1} = \frac{x_{\text{bitumen}}}{\rho_{\text{bitumen}}} + \frac{x_{\text{water}}}{\rho_{\text{water}}} + \frac{x_{\text{WCS}}}{\rho_{\text{WCS}}} \qquad (45)$$

The relation between emulsion density and composition in presence of solids is outlined in equation 46. In some embodiments, emulsion density is generated in block 331, and reference bitumen, water and phantom component (e.g. WCS) densities are generated in block 311. In some embodiments, solid density may be deemed to be 2320 kg/m³ which is the density of silica (sand).

$$\rho_{\text{emulsion}}^{-1} = \frac{x_{\text{bitumen}}}{\rho_{\text{bitumen}}} + \frac{x_{\text{water}}}{\rho_{\text{water}}} + \frac{x_{\text{WCS}}}{\rho_{\text{WCS}}} + \frac{x_S}{\rho_S} \qquad (46)$$

The relation between emulsion density and composition in presence of free gas is outlined in equation 47. In some embodiments, emulsion density is generated in block 331, and reference bitumen, water and phantom component (e.g. WCS) densities are generated in block 311. In some embodiments, free gas may be deemed to be saturated steam at wellhead conditions and so its density is calculated using equation 48 and 49

$$\rho_{\text{emulsion}}^{-1} = \frac{x_{\text{bitumen}}}{\rho_{\text{bitumen}}} + \frac{x_{\text{water}}}{\rho_{\text{water}}} + \frac{x_{\text{WCS}}}{\rho_{\text{WCS}}} + \frac{x_{\text{gas}}}{\rho_{\text{gas}}} \qquad (47)$$

$$\rho_{\text{gas}} = 322 \times \exp\left(-2.03\tau^{\frac{1}{3}} - 2.68\tau^{\frac{2}{3}} - 5.386\tau^{\frac{4}{3}} - 17.30\tau^3 - 44.76\tau^{\frac{37}{6}} - 63.92\tau^{\frac{71}{6}}\right) \qquad (48)$$

$$\tau = 1 - \frac{T_{\text{wellhead}}}{647.1} \qquad (49)$$

At 322, the system generates a produced fluid viscosity. In some embodiments, the system aspects for generating the produced fluid density at 321 include a neural network such as a convolutional neural network. In some embodiments, the neural network is trained to perform overlapping viscosity estimation analyses. In some embodiments, in an effort to achieve a faster convergence, the neural network includes a selector that receives a produced fluid contaminant (e.g. gas/solid/no-contaminant) signal from the emulsion density ARC and only awakens the neuron(s) corresponding to the ARC signal. In some embodiments 1 or 2 neuron branches can be activated.

Figure 13:
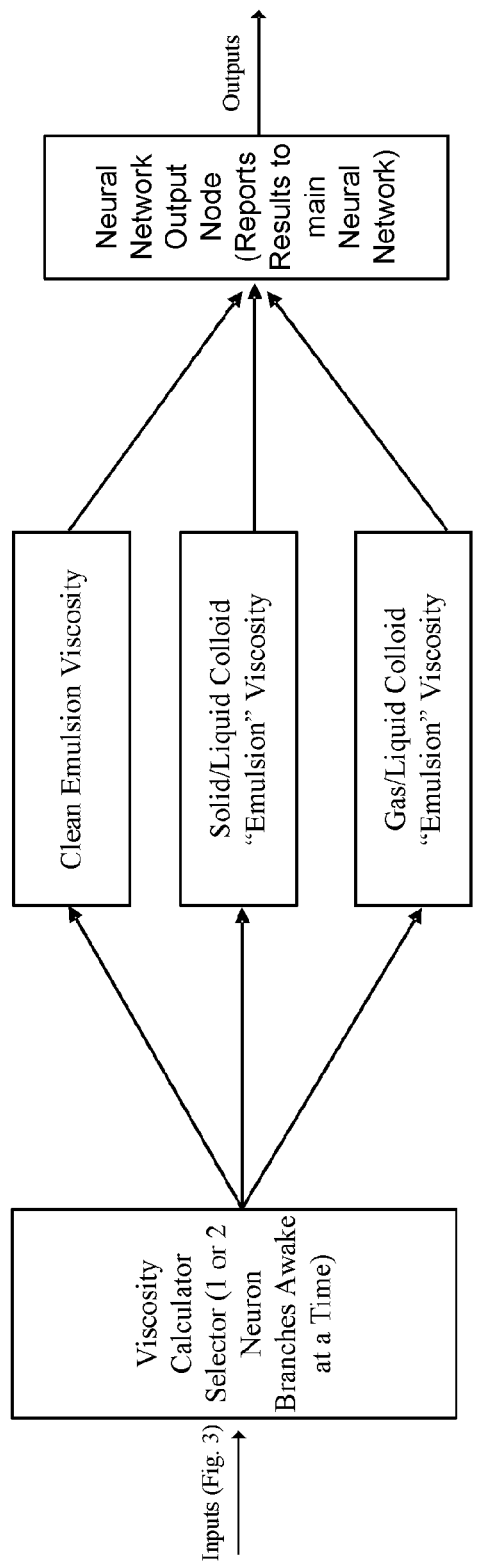
FIG. 13 is a flowchart illustrating aspects of an example neural network for generating produced fluid viscosity.

FIG. 13 shows aspects of an example neural network including the three neural network branches which may be selected by the produced fluid contaminant signal.

The emulsion viscosity philosophy is that hydrocarbon and water phases always exist as an emulsion in the system with any present contaminant free gas or solid turning the mixture into a colloid with water-hydrocarbon emulsion acting as the dispersant phase and free gas/solid acting as the dispersed phase. Therefore, in some embodiments, the clean emulsion viscosity neuron always calculates the viscosity of the water-hydrocarbon emulsion and reports the calculation results to the CNN's selector. This selector then uses the emulsion density ARC's contamination signal to decide if solids or free gas neurons have to be awaken to adjust the emulsions viscosity.

Three neurons embedded in this CNN calculate the viscosity of a clean emulsion (i.e. an emulsion with no free gas or solids), an emulsion contaminated with free gas, and an emulsion contaminated with solids using the emulsion composition node's data.

Asphaltene and resins act as surfactants in water-hydrocarbon emulsion. Therefore, based on Bancroft's role of thumb, which states that the phase in which surfactant dissolves preferably constitutes the emulsion's continuous phase, hydrocarbon must constitute the emulsion's continuous phase. However, emulsion viscosities calculated based on this observation are significantly higher than emulsion's measured viscosities. This inconsistency is resolved by treating the emulsion as a water-hydrocarbon-water emulsion. Thus, the viscosity of this emulsion is calculated in four steps. First, maximum water and hydrocarbon droplet diameters in this emulsion are calculated by the system. Second, these diameters are used by the system to estimate the fraction of emulsion water present in the bitumen phase as droplets. Third, this fraction is used by the system to calculate the bitumen phase's viscosity. Finally, bitumen phase's viscosity is used to calculate emulsion's viscosity given its composition.

In some instances, this approach may not fully address the peculiarities observed in emulsion viscosity calculations. Due to bitumen's high viscosity and salt content, determination of emulsion's disperse and continuous phases is not clear cut. In other words, it may not be clear if emulsion's continuous phase is bitumen contaminated with water droplets and its dispersed phase is "free water" or vice versa. To further complicate the matter, neither of phases is dilute enough for its droplets to be assumed to be isolated from each other if that phase constitutes the dispersed phase. These two issues have to be mitigated for the sensor's model to be an accurate reflection of the wellhead state.

In some embodiments, the system includes a perception which, in some instances, may mitigate the first problem. In some embodiments, the Perception comprises or is configured to utilize a Bayesian machine learning algorithm. In some embodiments, the perceptron can perform two tasks. First, it may verify that, at each time point, the correct dispersed phases is selected by evaluating the validity of estimated emulsion compositions and changing the dispersed phase selection if required. Second, it monitors and stores past results, and updates future selections which may, in some instances, reduce the number of wrong dispersed phase selections that it performs.

The second problem is mitigated by using the Yaron & Gal-Or model of concentrated emulsions which accounts for interactions both between phases and between dispersed phase's droplets to estimate wellhead emulsion's viscosity. The first major assumption of this model is that the emulsion's Capillary Number, i.e. the relative effect of viscous forces vs. surface tension across the interfacial interface, is small. This assumption is valid in this study as the wellhead emulsion, and oil-in-water emulsions in general, have small Capillary Numbers due to their strong interfacial surface tensions. The second major assumption of this model is that both phases of emulsion are Newtonian fluids. This assumption is valid in this study since water is a Newtonian fluid and bitumen behaves as Newtonian fluid at high temperatures experienced by the wellhead emulsion. In summary, Yaron & Gal-Or model of concentrated emulsions is used to estimate emulsion viscosity as neither of emulsion's water or hydrocarbon phases are dilute enough to deem droplets formed from it to be isolated from each other.

Equation 50 provides an estimation of maximum dispersed phase droplet diameter in an emulsion formed in a viscous turbulent fluid. The system evaluates this equation twice with one evaluation performed for water in hydrocarbon emulsion (i.e. the inner emulsion) and the other performed for hydrocarbon in water emulsion (i.e. the outer emulsion). $C_1$ and $C_2$ are constants equal to 0.7 and 2 respectively. Estimates of dispersed phase viscosities and densities are received from blocks 311, 313 and 314. Derivations of general formulas for calculating turbulent flow energy dissipation rate and hydrocarbon-water interfacial tension are described herein.

$$d_D = \left(\frac{4}{C_1 C_2}\right)^{3/5} \left(1 + \frac{C_2^{0.5} \mu_{Dispersed} \varepsilon^{1/3} d_D^{1/3}}{4\sigma_{W-HC}}\right) \sigma_{W-HC}^{3/5} \rho_{Continuous}^{-3/5} \varepsilon^{-2/5} \quad (50)$$

Equation 51 and 52 outline the general formulas used to estimate a mixture's interfacial tension. While these equations were originally developed for spherical molecules, they provide valid approximations for non-spherical molecules as well. Utilizing these equations require the knowledge of water and hydrocarbon's surface tensions along with their molar volumes. Molar volumes of water and hydrocarbon are calculated using equations 53 and 54 and density estimates are obtained by processes as described for blocks 311 and 314. In some instances, the system is configured to presume water molar mass to be about 18 g/mol and molar mass of hydrocarbon to be about 607 g/mol. Water's surface tension is well examined and its value at different temperatures is calculated using equation 55. A similar temperature-surface tension correlation is generated for hydrocarbon by fitting hydrocarbon surface tension of 0.026 J/m² at 23° C. into equation 56, which is derived on the basis of principle of corresponding states, to generate equation 57. Equation 56 is a modification of its original form with all of its original form's melting temperatures and molar volumes replaced by critical temperature and molar volumes. This is done per the principle of corresponding states and as hydrocarbon has a softening point instead of a melting point. For purposes of this equation, hydrocarbon's pseudo-critical temperature is deemed to be 1022° C.

$$\sigma_{W-HC} = \sigma_W + \sigma_{HC} - 2\Omega(\sigma_W \sigma_{HC})^{0.5} \quad (51)$$

$$\Omega = \frac{4 V_W^{1/3} V_{HC}^{1/3}}{(V_{HC}^{1/3} + V_{HC}^{1/3})} \quad (52)$$

$$V_W = \frac{M_W}{\rho_W} = \frac{0.018}{\rho_W} \quad (53)$$

$$V_B = \frac{M_B}{\rho_B} = \frac{\frac{0.607 x_B + 0.491 x_{WCS}}{x_B + x_{WCS}}}{\rho_{HC}} \quad (54)$$

-continued $$\sigma_W = 0.2358\left[\frac{647.15-T}{647.15}\right]^{1.256}\left[1-0.625\left(\frac{647.15-T}{647.15}\right)\right] \quad (55)$$

$$\sigma_{HC} = 2.746 \times 10^{24} \quad (56)$$

$$\frac{k[=1.858\times10^{-32}]T_C[=1022]}{V_{HC-C}[=0.00197]}\left[1-0.13\left(\frac{T}{T_c[=1022]}-1\right)\right]^{1.67} \rightarrow$$

$$\sigma_{HC} = 0.0265\left[1-0.13\left(\frac{T}{1022}-1\right)\right]^{1.67} \quad (57)$$

Equation 58 provides an approximation of the emulsion's turbulent flow energy dissipation rate. Most of the relevant energy dissipation occurs between ESP's discharge and choke valve. Therefore, fluid pressure required for this equation is calculated using equation 59 and fluid's effective volume is calculated using equation 60 with the rest of variables being read off of their respective data streams.

$$\varepsilon = \frac{PF}{\rho_{continuous} V_{Eff}} \quad (58)$$

$$P = \frac{1}{2}(P_{ESP\ Discharge}\ [\text{From Eq. 128}] + P_{Wellhead}) \quad (59)$$

$$V_{Eff} = \pi R_{prod\ string}^2 z_{ESP-MD} \quad (60)$$

Wellhead emulsion is a water-hydrocarbon-water emulsion with some of emulsion's water existing as a dispersed phase within the emulsion's hydrocarbon phase which itself exists as a dispersed phase in the remaining portion of emulsion's water. Looking at the emulsion's travel from wellbore to wellhead, it is logical to claim that emulsion exits the wellbore's ESP as a well-mixed solution due to ESP's high speed. From here towards the wellhead, emulsion evolves into a water-hydrocarbon-water emulsion that minimizes the total amount of its interfacial free energy. Denoting the fraction of emulsion's water existing as droplets in hydrocarbon with Y, this free energy is defined as equation 61 and 62 with different parts of these equations described below. The reference state from which this equation is defined is water and hydrocarbon existing as completely separate phases.

$$\Delta G_{IF} = \Delta W_{Water\ Droplet} + \Delta W_{HC\ Droplet} - T\Delta S \quad (61)$$

$$\Delta G_{IF} = W_{Water\ Droplet-Final} + W_{HC\ Droplet-Final} - W_{Initial} - T(S_{Emulsion} - S_{Reference}) \quad (62)$$

Total energy of interfacial tension created by water droplets is calculated using equation 63 with equation 64 providing an estimate of total surface area of water droplets suspended in hydrocarbon. Substituting equation 64 into equation 63 leads to equation 65 which provides an estimate of the total interfacial tension created by the formation water droplets as a function of the portion of emulsion's total water represented by those droplets.

$$W_{Water\ Droplet-Final} = a_{Water\ Droplet}\sigma_{W-B} \quad (63)$$

$$A_{Water\ Droplet} \frac{V_{Total}}{V_{Droplet}} A_{Droplet} = \left(\frac{m_{Water}}{\rho_{Water}}\right)\left(\frac{1}{6}\pi d_{d-w}^3\right)^{-1}(\pi d_{d-w}^2) = \frac{6Yx_{Water}}{\rho_{Water}d_{d-w}} \quad (64)$$

$$W_{Water\ Droplet-Final}(Y) = \left[\frac{6\sigma_{W-B}x_{Water}}{\rho_{Water}d_{d-W}}\right]Y \quad (65)$$

Total energy of interfacial tension created by hydrocarbon droplets is calculated using equation 66. The total volume of hydrocarbon phase is deemed to be equal to sum of volumes of water and hydrocarbon droplets as it is assumed that all of water droplets are suspended in the hydrocarbon phase. Therefore, equation 67 provides an estimate of hydrocarbon droplets total surface area. Combining equations 67 and 66 leads to equation 68. This equation provides an estimate of the total interfacial tension created by the formation of hydrocarbon droplets as a function of the portion of emulsion's total water represented by water droplets present in the hydrocarbon phase.

$$W_{HC\ Droplet-Final} = A_{HC\ Droplet}\sigma_{W-HC} \quad (66)$$

$$A_{HC\ Droplet} = \frac{V_{Total}}{V_{Droplet}}A_{Droplet} = \left(\frac{m_{Water}}{\rho_{Water}} + \frac{m_{HC}}{\rho_{HC}}\right)\left(\frac{1}{6}\pi d_{d-HC}^3\right)^{-1}(\pi d_{d-HC}^2) \quad (67)$$

$$= \left(\frac{Yx_{Water}}{\rho_{Water}} + \frac{x_B + x_{WCS}}{\rho_{HC}}\right)\left(\frac{6}{d_{d-HC}}\right)$$

$$W_{HC\ Droplet-Final}(Y) = \left(\frac{Y}{\rho_{Water}} + \frac{x_B + x_{WCS}}{\rho_{HC}}\right)\left(\frac{6\sigma_{W-HC}}{d_{d-HC}}\right) \quad (68)$$

$$= \left[\frac{6\sigma_{W-HC}x_{Water}}{d_{d-HC}\rho_{Water}}\right]Y + \left[\frac{6\sigma_{W-HC}(x_B + x_{WCS})}{d_{d-HC}\rho_{HC}}\right]$$

Figure 15:
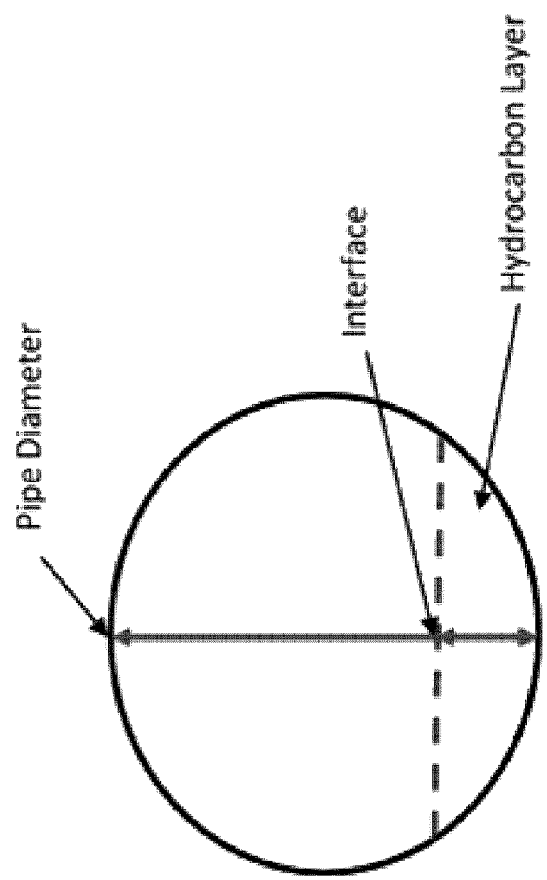
FIG. 15 is a cross section of a wellhead pipe when an emulsion is at its reference state.

Reference interfacial tension of the system is equal to the interfacial tension of the emulsion in the wellhead pipe with emulsion's water and hydrocarbon being completely separate from each other as shown in FIG. 15. Equations 69 and 70 are developed based on this figure and a series of calculations to create a relationship between reference state's unit interface area and emulsion's water content. These equations are combined with equation 71 to calculate the reference interfacial tension of the system.

$$R_{HC} = 0.001 \times \exp\left[\frac{\left(\frac{\rho_{Emulsion}}{\rho_{HC}}\right)(\pi R_{Pipe}^2)(1-x_{water})-0.69\ln(10^3 \times R_{Pipe})}{1.449}\right] \quad (69)$$

$$A_{Interface-Reference} = 2\left[\frac{\pi R_{Pipe}^2}{\rho_{Emulsion}}\right]\left[\sqrt{R_{HC}(2R_{Pipe}-R_{HC}^2)}\right] \quad (70)$$

$$W_{Initial} = \sigma_{W-HC}A_{Interface-Reference} \quad (71)$$

It is assumed that emulsion temperature and pressure at wellhead are constants and that material losses are negligible. Therefore, only water and hydrocarbon droplets' surface areas can change to accommodate changes in emulsion's interfacial Gibbs energy (i.e. equation 61). This means that emulsion's interfacial entropy can be calculated using equation 72 in which $S_A$ refers to entropy per unit area. The entropy per surface area value required for this equation is calculated using equation 73 which is based on the premise that surface tension is equal to the interface's Gibbs free energy per unit area. Since pressure and total interface areas are deemed to be constant in the partial derivative outlined by equation 73, derivative of the Guggenheim-Katayama equation, outlined in equation 74, is used to calculate the interface's unit entropy as outlined in equation 75. Values of n and $\sigma_{W-B}^o$ are estimated by fitting equation 74 into hydrocarbon-water interfacial tension values obtained at different temperatures for the emulsion composition under consideration using equations 51 to 57. Combining equation 74 with equation 73 and 72 leads to equation 75 which provides an estimate of interfacial entropy per unit area in the emulsion. Substituting this equation along with equations 67 and 64 into equation 72 leads to equation 76 which provide an estimate of emulsion's interfacial entropy.

$$S_{Emulsion} = S_A(A_{Water\ Droplet} + A_{HC\ Droplet}) \tag{72}$$

$$S_A = -\left(\frac{\delta \sigma_{W-HC}}{\delta T}\right)_{Area,P} \tag{73}$$

$$\sigma_{W-HC} = \sigma_{W-HC}^o \left(1 - \frac{T}{\varpi}\right)^n \tag{74}$$

$$S_A = \frac{\sigma_{W-HC}^o}{T_C}(n)\left(1 - \frac{T}{\varpi}\right)^{n-1} \tag{75}$$

$$S_{Emulsion} = \frac{\sigma_{W-HC}^o}{T_C}(n)\left(1 - \frac{T}{\varpi}\right)^{n-1}\left(\frac{12Y x_{Water}}{\rho_{Water} d_{d-W}} + \frac{6 x_{HC}}{\rho_{HC} d_{d-HC}}\right) \tag{76}$$

Emulsion's reference state entropy is calculated using the same principles used to calculate emulsion's current entropy with area terms replaced by reference state interfacial area terms outlined in equations 69 and 70. Therefore, equations 77 to 79 are used to calculate emulsion's reference state entropy.

$$R_{Bit} = 0.001 \times \exp\left[\frac{\left(\frac{\rho_{Emulsion}}{\rho_{Bit}}\right)(\pi R_{Pipe}^2)(1 - x_{water}) -}{\frac{0.609\ln(10^3 \times R_{Pipe})}{1.449}}\right] \tag{77}$$

$$A_{Interface-Reference} = 2\left[\frac{\pi R_{Pipe}^2}{\rho_{Emulsion}}\right]\left[\sqrt{R_{Bit}(2R_{Pipe} - R_{Bit}^2)}\right] \tag{78}$$

$$S_{Reference} = \frac{\sigma_{W-B}^o}{T_C}(n)\left(1 - \frac{T}{\varpi}\right)^{n-1}(A_{Interface-Reference}) \tag{79}$$

To calculate interfacial Gibbs energy, equations 79, 76, 71, 68, and 65 are substituted into equation 62 to generate equations 80 and 81. Since the objective is to estimate the fraction of emulsion water present as droplets (i.e. Y) at wellhead where emulsion is deemed to be at equilibrium, equations 80 and 81 are manipulated into equations 82 and 83 by substituting zero for $\Delta G_{IF}$ and solving for Y. These two equations provide an estimate of the mass fraction of emulsion water present as droplets in emulsion's hydrocarbon phase.

$$\Delta G_{IF} = \left[\frac{12\sigma_{W-B} x_{Water}}{\rho_{Water} d_{d-W}}\right] Y + \tag{80}$$
$$\left[\frac{6\sigma_{W-B} x_B}{d_{d-B}\rho_B}\right] - \sigma_{W-B} A_{Interface-Reference} - T\left(\frac{n\sigma_{W-B}^o}{\varpi}\left(1 - \frac{T}{\varpi}\right)^{n-1}\right.$$
$$\left.\left(\frac{12Y x_{Water}}{\rho_{Water} d_{d-W}} + \frac{6 x_B}{\rho_B d_{d-B}} - A_{Interface-Reference}\right)\right)$$

$$A_{Interface-Reference} = 2\left[\frac{\pi R_{Pipe}^2}{\rho_{Emulsion}}\right]\left[\sqrt{R_{Bit}(2R_{Pipe} - R_{Bit}^2)}\right] \tag{81}$$

$$Y = \left\{\sigma_{W-B} A_{Interface-Reference} - \left[\frac{6\sigma_{W-B} x_B}{d_{d-B}\rho_B}\right] + \right. \tag{82}$$
$$\frac{n\sigma_{W-B}^o T}{\varpi}\left(1 - \frac{T}{\varpi}\right)^{n-1}\left(\frac{6 x_B}{\rho_B d_{d-B}} - A_{Interface-Reference}\right)\right\}$$
$$\left\{\left[\frac{12\sigma_{W-B} x_{Water}}{\rho_{Water} d_{d-W}}\right] - T\left(\frac{n\sigma_{W-B}^o}{\varpi}\left(1 - \frac{T}{\varpi}\right)^{n-1}\left(\frac{12Y x_{Water}}{\rho_{Water} d_{d-W}}\right)\right)\right\}^{-1}$$

$$A_{Interface-Reference} = 2\left[\frac{\pi R_{Pipe}^2}{\rho_{Emulsion}}\right]\left[\sqrt{R_{Bit}(2R_{Pipe} - R_{Bit}^2)}\right] \tag{83}$$

In some embodiments, the hydrocarbon phase viscosity is based on the Yaron & Gal-Or model and equations 84 to 87. Hydrocarbon phase consists of hydrocarbon acting as the continuous phase and a fraction of emulsion's water existing as droplets acting as the dispersed phase. Volumetric fraction of these droplets are calculated using equation 84.

$$\Gamma = \left(\phi_{Dispersed}^{\frac{1}{3}}\right) \tag{84}$$
$$= \left(\frac{V_{Droplet}}{V_{HC} + V_{Droplet}}\right)^{\frac{1}{3}}$$
$$= \left(\frac{\frac{Y x_{water}}{\rho_{water}}}{\frac{x_B + x_{WCS}}{\rho_{HC}} + \frac{Y x_{water}}{\rho_{water}}}\right)^{\frac{1}{3}}$$

$$\kappa = \frac{\mu_{Dispersed}}{\mu_{Continuous}} = \frac{\mu_{Water}}{\mu_{HC}} \tag{85}$$

$$I(\Gamma, \kappa) = \frac{5.5[4\Gamma^7 + 10 - 7.636\Gamma^2 + 4\kappa^{-1}(1 - \Gamma^7)]}{10(1 - \Gamma^{10}) - 25\Gamma^3(1 - \Gamma^4) + 10\kappa^{-1}(1 - \Gamma^3)(1 - \Gamma^7)} \tag{86}$$

$$\mu_{Hydrocarbon\ Phase} = \mu_{Continuous}[1 + I(\Gamma, \kappa)\phi_{Dispersed}] \tag{87}$$
$$= \mu_{HC}[1 + I(\Gamma, \kappa)\phi_{Dispersed}]$$

In some embodiments, the clean emulsion viscosity is based on the Yaron & Gal-Or model and equations 88 to 91. Overall emulsion consists of hydrocarbon acting as the dispersed phase and a fraction of emulsion's water existing as "free water" acting as the continuous phase. Volumetric fraction of hydrocarbon phase is calculated using equation 88.

$$\Gamma = \left(\phi_{Dispersed}^{\frac{1}{3}}\right) \tag{88}$$
$$= \left(\frac{V_{Droplet}}{V_{HC} + V_{Droplet}}\right)^{\frac{1}{3}}$$
$$= \left(\frac{\frac{Y x_{water}}{\rho_{water}} + \frac{x_B + x_{WCS}}{\rho_{HC}}}{\frac{x_B + x_{WCS}}{\rho_{HC}} + \frac{x_{water}}{\rho_{water}}}\right)^{\frac{1}{3}}$$

$$\kappa = \frac{\mu_{Dispersed}}{\mu_{Continuous}} = \frac{\mu_{Water}}{\mu_{HC}} \tag{89}$$

$$I(\Gamma, \kappa) = \frac{5.5[4\Gamma^7 + 10 - 7.636\Gamma^2 + 4\kappa^{-1}(1 - \Gamma^7)]}{10(1 - \Gamma^{10}) - 25\Gamma^3(1 - \Gamma^4) + 10\kappa^{-1}(1 - \Gamma^3)(1 - \Gamma^7)} \tag{90}$$

-continued $$\mu_{Bitumen\ Phase} = \mu_{Continuous}[1 + I(\Gamma, \kappa)\phi_{Dispersed}] \quad (91)$$
$$= \mu_{HC}[1 + I(\Gamma, \kappa)\phi_{Dispersed}]$$

In some embodiments, when the system determines the viscosity of an emulsion contaminated with solids, the system may assume that a solids particles present in the emulsion are uniformly distributed within it due to the high agitation rate imposed on the flow from wellbore to wellhead. Under this assumption, emulsion viscosity calculated by the clean emulsion viscosity neuron is adjusted to account for presence of solids using the Thomas modification of Einstein's formula for effective slurry viscosity as outlined in equations 92 and 93.

$$\mu_{emulsion} = \mu_{clean\ emulsion}\begin{bmatrix} 1 + 2.5\phi_{solids} + 10.05\phi_{solids}^2 + \\ 0.00273\exp(16.6\phi_{solids}) \end{bmatrix} \quad (92)$$

$$\phi_{solids} = \frac{V_{solids}}{V_{Total}} \quad (93)$$
$$= \frac{\frac{x_S}{\rho_S}}{\frac{1}{\rho_{emulsion}}}$$
$$= \frac{\rho_{emulsion}}{2320}x_S$$

In some embodiments, when the system determines the viscosity of an emulsion contaminated with free gas, the system may assume that free gas bubbles are uniformly distributed within the emulsion due to high agitation rate imposed by the emulsion flow. It is also assumed that emulsion is isothermal from wellhead to choke valve due to the short distance between these points and installed heat insulation material. Moreover, as discussed above, emulsion's Capillary Number is low. Therefore, based on all these points, gas bubbles present in emulsion are spherical and so Taylor's formula for calculation of viscosity in colloids with highly deformable dispersed phase, which free gas is, is used to adjust clean emulsion's viscosity for presence of free gas. This formula is outlined in equations 94 to 97. Emulsion density is calculated by the ARC at block 331. Free gas is assumed to consist entirely of steam and hence its viscosity is calculated using the Sutherland equation as outlined in equation 98 and 99. While Sutherland's equation is generally suited for ideal gases, its application to steam is well-known and is with acceptable accuracy. No pressure term is included in this calculation as gas viscosity is, in general, independent of pressure. Finally, Free gas density is calculated using equations 48 and 49.

$$\mu_{emulsion} = \mu_{clean\ emulsion}(1 + f\phi_{free\ gas}) \quad (94)$$

$$f = \frac{5\lambda_{free\ gas} + 2}{2(\lambda_{free\ gas} + 1)} \quad (95)$$

$$\lambda_{free\ gas} = \frac{\mu_{free\ gas}}{\mu_{clean\ emulsion}} \quad (96)$$

$$\phi_{free\ gas} = \frac{V_{free\ gas}}{V_{Total}} \quad (97)$$
$$= \frac{\frac{x_{free\ gas}}{\rho_{free\ gas}}}{\frac{1}{\rho_{emulsion}}}$$
$$= \frac{\rho_{emulsion}}{\rho_{free\ gas}}x_{free\ gas}$$

$$\mu_{steam} = \mu_{ref}\frac{T_{ref} + C}{T + C}\left(\frac{T}{T_{ref}}\right)^{1.5}\ \underline{\mu_{ref} = 1.227 \times 10^{05}\ Pa\cdot s\ \text{at 373 }K} \quad (98)$$

$$\mu_{steam} = 1.227 \times 10^{-5}\frac{1334}{T + 961}\left(\frac{T}{373}\right)^{1.5} \quad (99)$$

At 323, the system generates the emulsion composition. In some embodiments, the system includes 3 outputs (emulsion water, bitumen, and phantom component contents) which can be based on three independent set of equations (composition-density relationship, composition-choke valve performance relationship, and emulsion mass balance). This means that it cannot necessarily produce an emulsion composition estimation that satisfies all of the three independent equation sets. Moreover, all three independent equation sets rely on potentially noisy and error laden data which means that none is significantly more accurate than the other. Thus, the sensor has to estimate the emulsion composition using an approach that treats all equations sets equally and finds an emulsion composition estimate that reasonably satisfies all of them.

In some embodiments, the system includes an iterative convergence tool such as a processor or other component configured to operate a Gauss-Newton process. In some embodiments, to reduce computation time and/or to enhance the convergence rate of the process, the Gauss-Newton algorithm is directly used to estimate emulsion's bitumen and water contents while emulsion's phantom component (e.g. WCS) content is calculated using equation 100 which is based on emulsion's mass balance. Minimum WCS content of 0.001 may be chosen to prevent a division by zero fatal error from happening in the Hydrocarbon Phase Viscosity neuron.

$$x_{WCS,i} = \text{Max}(1 - x_{B,i} - x_{W,i}, 0.001) \quad (100)$$

In some embodiments, the iterative convergence tool proceeds toward the optimal composition using an iterative process in which the j+1 composition estimate is calculated from the j estimate using equation 101 which is shown in full details in equation 102. Terms outlined in equation 102 are calculated using equations 103 to 106. Combination of equations 101 to 106 with each other leads to equations 107 and 108 that calculate the j+1 composition estimate from the j one. A damping factor of 0.1 is used in these equations to ensure a smoother convergence toward the optimal emulsion composition.

$$X'_{j+1} = X'_j - (J_r)^{-1}R(X'_j) \quad (101)$$

-continued $$\begin{bmatrix} x_{bitumen,j+1} \\ x_{water,j+1} \end{bmatrix} = \begin{bmatrix} x_{bitumen,j} \\ x_{water,j} \end{bmatrix} - \quad (102)$$

$$\frac{1}{\frac{\delta r_1}{\delta x_{bitumen,j}} \frac{\delta r_2}{\delta x_{water,j}} - \frac{\delta r_1}{\delta x_{water,j}} \frac{\delta r_2}{\delta x_{bitumen,j}}}$$

$$\begin{bmatrix} \frac{\delta r_2}{\delta x_{water,j}} & -\frac{\delta r_1}{\delta x_{water,j}} \\ -\frac{\delta r_2}{\delta x_{bitumen,j}} & \frac{\delta r_1}{\delta x_{bitumen,j}} \end{bmatrix} \begin{bmatrix} r_1(X_j) \\ r_2(X_j) \end{bmatrix}$$

$$r_1(X_j) = \rho_{emulsion\ calculated}(X_j) - \rho_{emulsion\ measured} \quad (103)$$

$$r_2(X_j) = \mu_{emulsion\ calculated}(X_j) - \mu_{emulsion\ measured} \quad (104)$$

$$\frac{\delta r_i}{\delta x_{bitumen,j}} = \frac{r_i(x_{bitumen,j} + 0.0005,\ \text{Rest Constant}) - r_i(x_{bitumen,j},\ \text{Rest Constant})}{0.0005} \quad (105)$$

$$\frac{\delta r_i}{\delta x_{water,j}} = \frac{r_i(x_{water,j} + 0.0005,\ \text{Rest Constant}) - r_i(x_{water,j},\ \text{Rest Constant})}{0.0005} \quad (106)$$

$$x_{bitumen,j+1} = \quad (107)$$

$$x_{bitumen,j} - \frac{\frac{\delta r_2}{\delta x_{water,j}} r_1(X_j) - \frac{\delta r_1}{\delta x_{water,j}} r_2(X_j)}{\frac{\delta r_1}{\delta x_{bitumen,j}} \frac{\delta r_2}{\delta x_{water,j}} - \frac{\delta r_1}{\delta x_{water,j}} \frac{\delta r_2}{\delta x_{bitumen,j}}} \times \text{Damping}$$

$$x_{water,j+1} = \quad (108)$$

$$x_{water,j} - \frac{-\frac{\delta r_2}{\delta x_{bitumen,j}} r_1(X_j) + \frac{\delta r_1}{\delta x_{water,j}} r_2(X_j)}{\frac{\delta r_1}{\delta x_{bitumen,j}} \frac{\delta r_2}{\delta x_{water,j}} - \frac{\delta r_1}{\delta x_{water,j}} \frac{\delta r_2}{\delta x_{bitumen,j}}} \times \text{Damping}$$

For emulsions contaminated with solids, the system can be similarly configured. However, since in this scenario the emulsion composition system is underdefined (four compositional variables and three independent equations), it is possible to calculate infinitely many emulsion compositions that minimize the system error with at least one of them having a zero overall residual (equation 44). Only a few of these many solutions may be valid estimates and these valid estimates do not have to have a zero overall residual. In some instances, many optimization algorithms such as the Gauss-Newton algorithm may converge toward an emulsion composition with the zero residual which may or may not be a valid solution. Therefore, in some embodiments, the system includes a two layered kernel machine to estimate the emulsion composition. This kernel's inner layer calculates emulsion's water, solid, and bitumen contents while its outer layer calculates its WCS content as described herein.

In some instances, the kernel machine may partially circumvent the under-definition problems through two techniques. First, in some embodiments, the kernel machine is configured to starts the current composition estimation using the previous iterations output (i.e. it parses for the current estimate starting from the old one). This way, its current composition estimate is one that both has a small overall residual and is close to the previous iteration's output. This applies a weak time based filter to emulsion composition that ensures that emulsion composition estimates calculated by the kernel machine vary gradually as to reflect the emulsion's actual behavior.

Second, in some embodiments, the kernel machine is configured to circumvents the under-definition problem by dividing the emulsion composition exercise into two parts with each part being completely defined. In some instances, this may reduce the possibility of calculation of unfeasible emulsion estimates as under-definition may not be an issue for the two individual parts.

The kernel machine's inner layer estimates emulsions water, solid, and bitumen contents without changing emulsion's phantom component (e.g. WCS) content using the Gauss-Newton algorithm and the matrix outlined in equation 109. Expansion of this matrix leads to equation 110 to 119 and table 1. It is critical to note that the inverse of equation 109's Jacobian matrix is calculated using Cramer's rule.

$$X'_{j+1} = X'_j - (J_r)^{-1} R(X'_j) \quad (109)$$

$$\begin{bmatrix} x_{bitumen,j+1} \\ x_{water,j+1} \\ x_{solids,j+1} \end{bmatrix} = \begin{bmatrix} x_{bitumen,j} \\ x_{water,j} \\ x_{solids,j} \end{bmatrix} - \begin{bmatrix} \Theta_1 & \Theta_2 & \Theta_3 \\ \Theta_4 & \Theta_5 & \Theta_6 \\ \Theta_7 & \Theta_8 & \Theta_9 \end{bmatrix} \begin{bmatrix} r_1(X_j) \\ r_2(X_j) \\ r_3(X_j) \end{bmatrix} \quad (110)$$

$$r_1(X_j) = \rho_{emulsion\ calculated}(X_j) - \rho_{emulsion\ measured} \quad (111)$$

$$r_2(X_j) = \mu_{emulsion\ calculated}(X_j) - \mu_{emulsion\ measured} \quad (112)$$

$$r_3(X_j) = x_{bitumen,j} + x_{water,j} + x_{solids,j} + x_{WCS,j} - 1 \quad (113)$$

$$\frac{\delta r_i}{\delta x_{bitumen,j}} = \frac{r_i(x_{bitumen,j} + 0.0005,\ \text{Rest Constant}) - r_i(x_{bitumen,j},\ \text{Rest Constant})}{0.0005} \quad (114)$$

$$\frac{\delta r_1}{\delta x_{water,j}} = \frac{r_i(x_{water,j} + 0.0005,\ \text{Rest Constant}) - r_i(x_{water,j},\ \text{Rest Constant})}{0.0005} \quad (115)$$

$$\frac{\delta r_1}{\delta x_{solids,j}} = \frac{r_i(x_{solids,j} + 0.0005,\ \text{Rest Constant}) - r_i(x_{solids,j},\ \text{Rest Constant})}{0.0005} \quad (116)$$

$$x_{bitumen,j+1} = x_{bitumen,j} - [\Theta_1 r_1(X_j) + \Theta_2 r_2(X_j) + \Theta_3 r_3(X_j)] \quad (117)$$

$$x_{water,j+1} = x_{water,j} - [\Theta_4 r_1(X_j) + \Theta_5 r_2(X_j) + \Theta_6 r_3(X_j)] \quad (118)$$

$$x_{solids,j+1} = x_{solids,j} - [\Theta_7 r_1(X_j) + \Theta_8 r_2(X_j) + \Theta_9 r_3(X_j)] \quad (119)$$

TABLE 1

Equation 110 Inverse Jacobian Matrix Terms

| Term | Formula |
|---|---|
| $\chi$ | $\frac{\delta r_1}{\delta x_B}\left(\frac{\delta r_2}{\delta x_W}\frac{\delta r_3}{\delta x_S} - \frac{\delta r_2}{\delta x_S}\frac{\delta r_3}{\delta x_W}\right) - \frac{\delta r_1}{\delta x_W}\left(\frac{\delta r_2}{\delta x_B}\frac{\delta r_3}{\delta x_S} - \frac{\delta r_2}{\delta x_S}\frac{\delta r_3}{\delta x_B}\right) + \frac{\delta r_1}{\delta x_S}\left(\frac{\delta r_2}{\delta x_B}\frac{\delta r_3}{\delta x_W} - \frac{\delta r_3}{\delta x_B}\frac{\delta r_2}{\delta x_W}\right)$ |
| $\Theta_1$ | $\left(\frac{\delta r_2}{\delta x_W}\frac{\delta r_3}{\delta x_S} - \frac{\delta r_3}{\delta x_W}\frac{\delta r_2}{\delta x_S}\right)\chi^{-1}$ |
| $\Theta_2$ | $-\left(\frac{\delta r_2}{\delta x_B}\frac{\delta r_3}{\delta x_S} - \frac{\delta r_2}{\delta x_S}\frac{\delta r_3}{\delta x_B}\right)\chi^{-1}$ |
| $\Theta_3$ | $\left(\frac{\delta r_2}{\delta x_B}\frac{\delta r_3}{\delta x_W} - \frac{\delta r_2}{\delta x_W}\frac{\delta r_3}{\delta x_B}\right)\chi^{-1}$ |
| $\Theta_4$ | $-\left(\frac{\delta r_1}{\delta x_W}\frac{\delta r_3}{\delta x_S} - \frac{\delta r_1}{\delta x_S}\frac{\delta r_3}{\delta x_W}\right)\chi^{-1}$ |
| $\Theta_5$ | $\left(\frac{\delta r_1}{\delta x_B}\frac{\delta r_3}{\delta x_S} - \frac{\delta r_1}{\delta x_S}\frac{\delta r_3}{\delta x_B}\right)\chi^{-1}$ |

TABLE 1-continued

Equation 110 Inverse Jacobian Matrix Terms

| Term | Formula |
|---|---|
| $\Theta_6$ | $-\left(\dfrac{\delta r_1}{\delta x_B}\dfrac{\delta r_3}{\delta x_W} - \dfrac{\delta r_1}{\delta x_W}\dfrac{\delta r_3}{\delta x_B}\right)\chi^{-1}$ |
| $\Theta_7$ | $\left(\dfrac{\delta r_1}{\delta x_W}\dfrac{\delta r_2}{\delta x_S} - \dfrac{\delta r_1}{\delta x_S}\dfrac{\delta r_2}{\delta x_W}\right)\chi^{-1}$ |
| $\Theta_8$ | $-\left(\dfrac{\delta r_1}{\delta x_B}\dfrac{\delta r_2}{\delta x_S} - \dfrac{\delta r_1}{\delta x_S}\dfrac{\delta r_2}{\delta x_B}\right)\chi^{-1}$ |
| $\Theta_9$ | $\left(\dfrac{\delta r_1}{\delta x_B}\dfrac{\delta r_2}{\delta x_W} - \dfrac{\delta r_1}{\delta x_W}\dfrac{\delta r_2}{\delta x_B}\right)\chi^{-1}$ |

The kernel machine's outer layer calculates an emulsion's phantom component (WCS) content by slightly adjusting emulsion's the non-WCS compositional estimates. However, to ensure machine stability, outer kernel does not adjust the relative ratio of non-WCS compounds' mass fractions with respect to each other. This machine estimates the emulsion's WCS content by attempting to minimize the residual function outlined in equation 120. This residual function is based on the fact the WCS is a phantom component, is used to adjust bitumen parameters for variations between reservoirs and between different times in a reservoir, and does not actually exist in the system. Therefore, in some embodiments, the emulsion's estimated WCS content is minimized to reduce the impact of this phantom component on the emulsion composition estimate. However, this minimization should not be done at the cost of imparting larger errors in the calculation of the emulsion composition estimate. Hence, minimizing equation 120 should provide a suitable trade-off between error imparted by having large WCS estimates and errors imparted by having unreasonably small WCS estimates. In some embodiments, the system may impose a maximum value for WCS as values about this maximum may represent unrealistic or unreliable results.

$$r_4(X_j) = |r_1(X_j)| + |r_2(X_j)| + |r_3(X_j)| + |x_{WCS}| \qquad (120)$$

In some embodiments, the kernel machine includes an iterative convergence tool for iteratively calculating the estimated produced fluid composition. In some embodiments, the kernel machine applies a Gauss-Newton algorithm. Iterative functions used to calculate emulsion's phantom component and non-phantom component contents are outlined in equation 121 & 122 and 123 respectively. Equation 123 is obtained by combining the fact that emulsion composition must always add up to one with the requirement that the outer kernel does not adjust the relative ratio of non-phantom component compounds' mass fractions with respect to each other.

$$x_{WCS,j+1} = x_{WCS,j} - \dfrac{r_4(X_j)}{\dfrac{\delta r_4(X_j)}{\delta x_{WCS}}} \qquad (121)$$

$$\dfrac{\delta r_4}{\delta x_{WCS,j}} = \dfrac{r_4(x_{WCS,j} + 0.0005,\ \text{Rest Constant}) - r_4(x_{WCS,j},\ \text{Rest Constant})}{0.0005} \qquad (122)$$

$$x_{All\ Excluding\ WCS,j+1} = x_{All\ Excluding\ WCS,j} \times \dfrac{1 - x_{WCS,j+1}}{1 - x_{WCS,j}} \qquad (123)$$

In some embodiments, the same or similar process for generating the composition of emulsion contaminated with solids is used to estimate the composition of emulsion contaminated with free gas. i.e. the process outlined above is adjusted with all solids related terms replaced with free gas terms.

Figure 14:
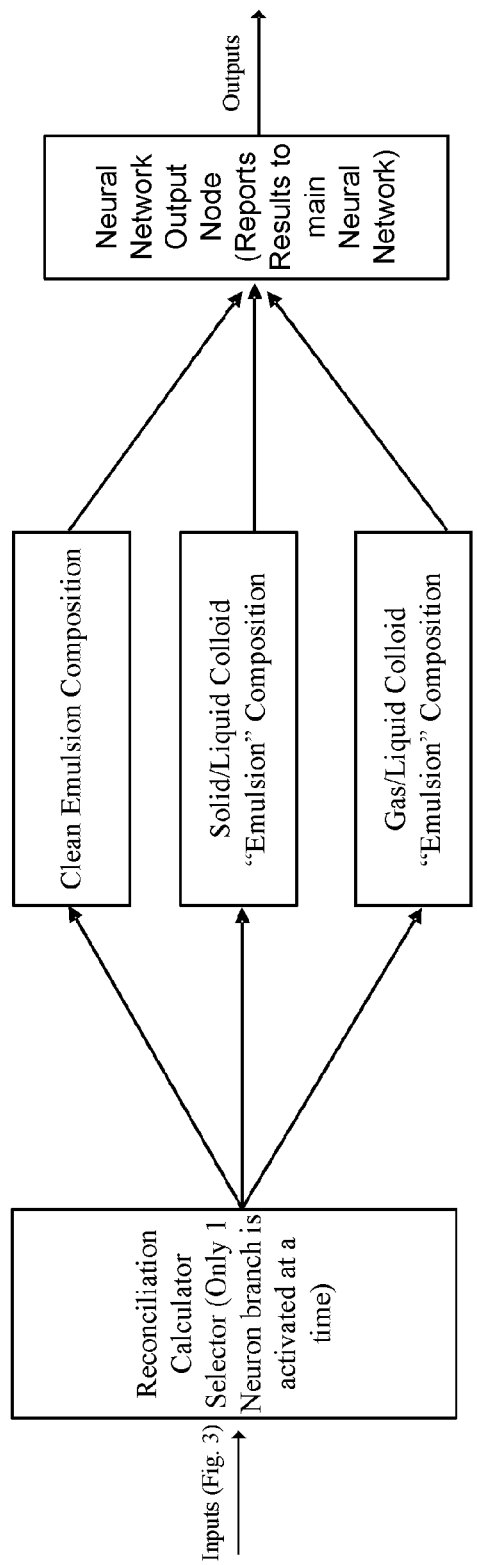
FIG. 14 is a flowchart illustrating aspects of an example neural network for generating produced fluid composition.

In some embodiments, the produced fluid composition generator includes a neural network. The neural network includes a selector that receives a produced fluid contaminant (e.g. gas/solid/no-contaminant) signal from the emulsion density ARC and only awakens the neuron(s) corresponding to the ARC signal. In some embodiments, three neurons/neuron sets/branches embedded in the neural network each determine the composition of a clean emulsion (i.e. an emulsion with no free gas or solids), an emulsion contaminated with free gas, and an emulsion contaminated with solids using the emulsion composition node's data and computations described above. FIG. 14 shows aspects of an example neural network including the three neural network branches which may be selected by the produced fluid contaminant signal.

Wellheads often have Coriolis density meters that are capable of providing estimates of emulsion density. However, these meters are not calibrated on a PM basis as they are not MARP (Measurement, Accounting, and Reporting Plan) meters. Thus, their readings may not be accurate.

With respect to block 331, in some embodiments, the system includes an advanced regulatory control (ARC) system which, in some instances, can check for presence of contaminants in the emulsion and/or minimizes invalid soft sensor outputs.

Figure 16:
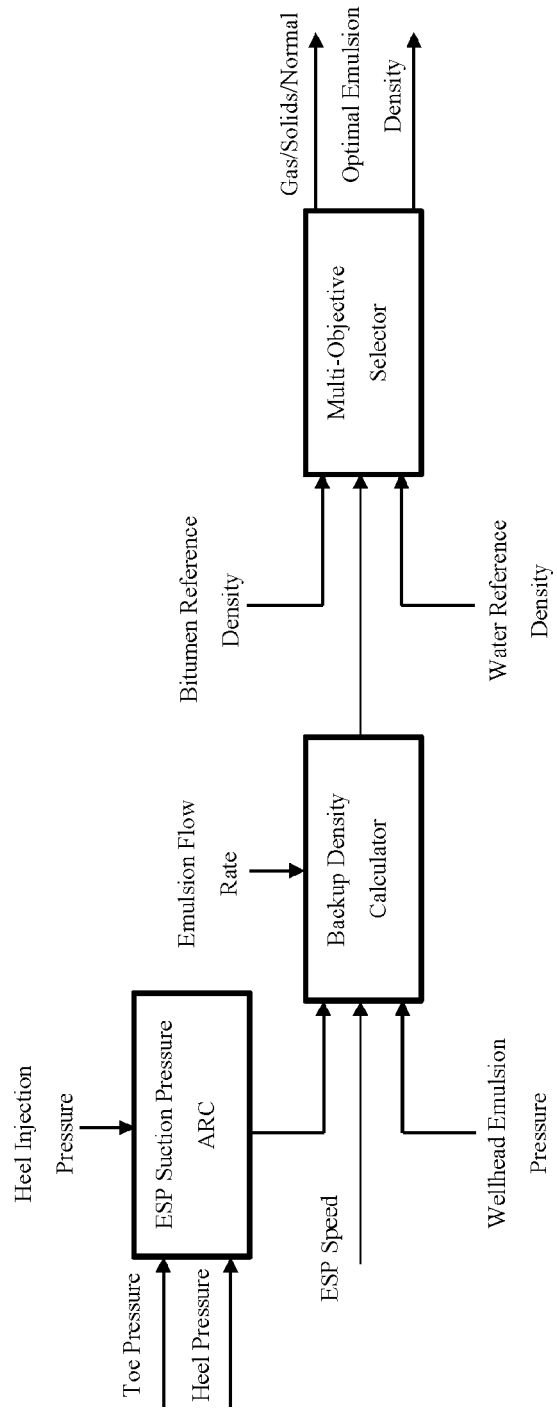
FIG. 16 is a flowchart illustrating aspects of an example produced fluid density advanced regulatory control system.

FIG. 16 shows a data flow diagram showing aspects of an example ARC system. In some embodiments, the ARC system includes a backup density calculator. In some instances, the backup density calculator is configured based on the fact that a pump's head is independent of the density the fluid that it is pumping. In some embodiments, the calculator generates the ESP's head, and the emulsion's pressure at the ESP discharge; and combines this data to generate a backup emulsion density.

In some embodiments, ESP head can be calculated using equations 124 to 126. These equations, sometimes referred to as the Walshaw-Jobson correlation system, relate the pump impeller speed, head, and flow rate. $\lambda_0$, $\lambda_1$, and $\lambda_2$ are obtained by fitting the Walshaw-Jobson system into the ESP's pump curve and the rest of variables are obtained from their respective DCS data streams. The original form of this system includes terms to include impeller diameter in the pump performance relationship matrix. However, these terms are left out as impeller diameter does not change during the course of operation of an ESP and thus its effect on the pump head-speed-flow matrix can easily be captured by $\lambda_0$, $\lambda_1$, and $\lambda_2$.

$$C_H = \dfrac{gH_{ESP}}{\omega^2} \qquad (124)$$

$$C_F = \dfrac{F}{\omega} \qquad (125)$$

$$C_H = \lambda_0 + \lambda_1 C_F + \lambda_2 C_F^2 \quad (126)$$

Emulsion pressure at pump discharge is calculated by adding the static pressure differential between ESP discharge and wellhead pressure transmitter and frictional pressure drop in the production string to wellhead pressure reading as outlined in equation 127. Emulsion frictional losses between ESP and wellhead are calculated using the Darcy-Weisbach formula outlined in equation 130. Substituting the relationship between emulsion velocity and flow rate into equation 129 has led to this equation. Darcy friction factor of 0.026 is used per Moody's diagram and the production string characteristics. Substituting this equation into equation 127 leads to equation 128.

$$p_{discharge} = p_{wellhead} + \rho_{emulsion} g z_{ESP-TVD} + \Delta p \quad (127)$$

$$p_{discharge} = \quad (128)$$
$$p_{wellhead} + \rho_{emulsion} g z_{ESP-TVD} + \left(\frac{0.208 L_{ESP-MD}}{\pi^2 D_{Prod.Str.}^5}\right) \rho_{Emulsion} F_E^2$$

$$\Delta p = f_d \cdot \frac{L_{ESP-MD}}{D_{Prod.Str.}} \cdot \frac{\rho_{Emulsion} v_E^2}{2} \quad (129)$$

$$\Delta p = \left(\frac{0.208 L_{ESP-MD}}{\pi^2 D_{Prod.Str.}^5}\right) \rho_{Emulsion} F_E^2 \quad (130)$$

$$\rho_{Emulsion} g H_{ESP} = p_{discharge} - p_{suction} \quad (131)$$

$$\rho_{emulsion} = \left[\frac{p_{wellhead} + \rho_{emulsion} g z_{ESP-TVD} +}{\left(\frac{0.208 L_{ESP-MD}}{\pi^2 D_{Prod.Str.}^5}\right) \rho_{Emulsion} F_E^2 - p_{suction}}\right]^{-1} [g H_{ESP}] \quad (132)$$

The suction pressure ARC uses the criterion outlined in equation 133 along with the latest optimal emulsion density estimate (or Coriolis meter reading if one is not available) to determine if a projected ESP suction pressure is valid or not. Essentially, this criterion is a check of whether the sum of ESP head and projected ESP suction pressure minus the expected static and frictional pressure drops between ESP and wellhead are close to the wellhead emulsion pressure, which they should be, or not. Projected ESP suction pressure sources are outlined in table 2 in order of their priority with ARC ruling out a higher ranked data source before moving to a lower ranked one.

$$\left| p_{ESPSuction} + \rho_{Emulsion} g H_{ESP} - \rho_{Emulsion} g z_{ESP-TVD} - \left(\frac{0.208 L_{ESP-MD}}{\pi^2 D_{Prod.Str.}^5}\right) \rho_{Emulsion} F_E^2 - p_{wellhead} \right| \leq 100 \, kPa \quad (133)$$

TABLE 2

ESP Suction Pressure Data Sources

| Rank | Source | Source | Notes |
|---|---|---|---|
| 1 | Producer Heel | $P_{heel}$ | |
| 2 | Producer Toe | $p_{toe} - \left(\frac{0.208[L_{toe-MD} - L_{ESP-MD}]}{\pi^2 D_{Producer}^5}\right) \rho_{Emulsion} F_E^2 -$ Corr. Factor $\times (z_{Toe-TVD} - z_{ESP-TVD})$ | Use scab liner diameter as producer well diameter if one is installed. Otherwise, use slotted liner diameter. Second correction term is obtained from MI3. |
| 3 | Injector Heel | $P_{Injector\,heel}$ | |

ESP head relation with emulsion's pressure differential across the ESP is outlined in equation 131. Discharge pressure calculation approach is outlined in previous parts of this section and emulsion pressure at ESP suction is calculated as described below. Substitution of equation 128 into this equation leads to equation 132. This equation can easily be solved to obtain a function explicit in terms of emulsion density. Nevertheless, an alternate approach is taken in which the latest calculated optimal emulsion density (or Coriolis meter reading if one is not available) is used for bolded emulsion terms. This approach is taken to convert the backup emulsion density calculation formula from one that satisfies the Markov property to one that resembles a Wiener process. This ensures that backup emulsion density is adequately filtered while not being overwhelmed by previous density estimates.

In some embodiments, the ARC includes a multi-objective selector. This selector checks whether wellhead Coriolis meter's emulsion density readings are in-between water and bitumen reference densities at process conditions. If they are not, selector replaces them with backup emulsion density readings only if backup emulsion density readings satisfy this criterion. If neither of emulsion density readings fulfill the validity criterion, a "solids" message is transmitted to the soft sensor if Coriolis meter density readings are larger than both reference densities. Otherwise, a "gas" message is transmitted if Coriolis meter density readings are smaller than both reference densities. Coriolis meter readings are not replaced with backup emulsion density estimations in these scenarios.

As described above, in some embodiments, the system includes a produced fluid perceptron (block 341). In some instances, the produced fluid's dispersed phase can constitute hydrocarbon or water phases that can impact the emulsion viscosity. If the selector selecting the wrong dispersed phase, the accuracy of estimated bitumen composition may be impacted. In some embodiments, the system is configured to generate the emulsion composition twice: once treating the hydrocarbon phase as the emulsion's dispersed phase and the other doing the opposite. With these composition outputs, the system determines which output is a valid emulsion composition, and the other output is discarded. In some instances, this may be computationally expensive to perform.

Figure 17:
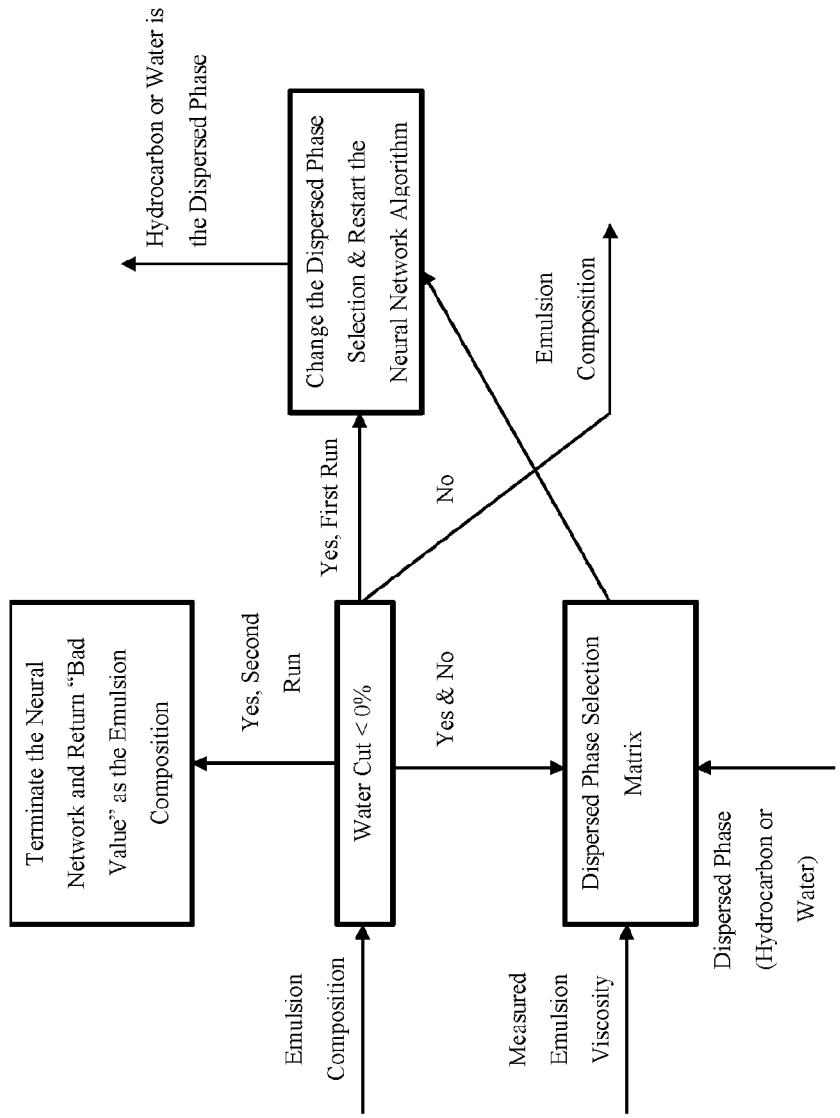
FIG. 17 is a flowchart illustrating aspects of an example produced fluid composition calculator QA/QC perceptron.

In another embodiment, the systems includes a machine learning system to predictively select the dispersed phase to reduce the computation requirements. In some embodiments, a Bayesian Perceptron is used to minimize the impact of wrong dispersed phase selection on DCS calculation load. The perceptron can include two parts: a first part performing on-spot QA/QC of emulsion data, and a second part using the QA/QC performance results to minimize the number of wrong dispersed phase selections. An overview of this system is provided in FIG. 17.

In some embodiments, the dispersed phase selection matrix is configured to optimize the selection of dispersed phase and minimize the number of wrong selections and resultant calculations. This matrix's setup is outlined in equation 134 and, in an example embodiments, it can be formatted as follows:

It covers viscosity measurements between 0 Pa·S and 100 Pa·S with rows 1 to 30 having 0.0002 intervals covering the overall viscosity range of 0 to 0.006 and row 31 having a 99.994 Pa·S interval covering a range covering the viscosity range of 0.006 Pa·S to 100 Pa·S.

# of Water Successes in each row is defined as the number of valid emulsion composition estimates that have been obtained by treating water as the emulsion's dispersed phase for wellhead emulsions with viscosities falling in that row's range.

# of Hydrocarbon Successes in each row is defined as the number of valid emulsion composition estimates that have been obtained by treating hydrocarbon as the emulsion's dispersed phase for wellhead emulsions with viscosities falling in that row's range.

# of Total Failures in each row is defined as the number of times that a "Bad Value" error has been returned by the Perceptron for wellhead emulsions with viscosities falling in that row's range.

This matrix is filled on the basis of a 30 day rolling database. i.e. the oldest entry used to fill out is 30 days old with new entries replacing old ones a continuous basis.

reports either of water of hydrocarbon that has the highest number of successful emulsion composition estimates as the emulsion's dispersed phase. This is done after calculation of emulsion's measured viscosity and before the start of the GN algorithm. Perceptron performs the second tasks by applying conditions outlined in FIG. 16 to data and either re-running the neural network with a new dispersed phase, accepting the calculated emulsion composition as a valid output or deeming the system insolvable if no valid emulsion composition estimate has been calculated from treatment of either of water or hydrocarbon as the emulsion's dispersed phases. In all these scenarios, Perceptron also updates the dispersed phase selection matrix using its decision-making's outcome and emulsion's viscosity.

Figure 18:
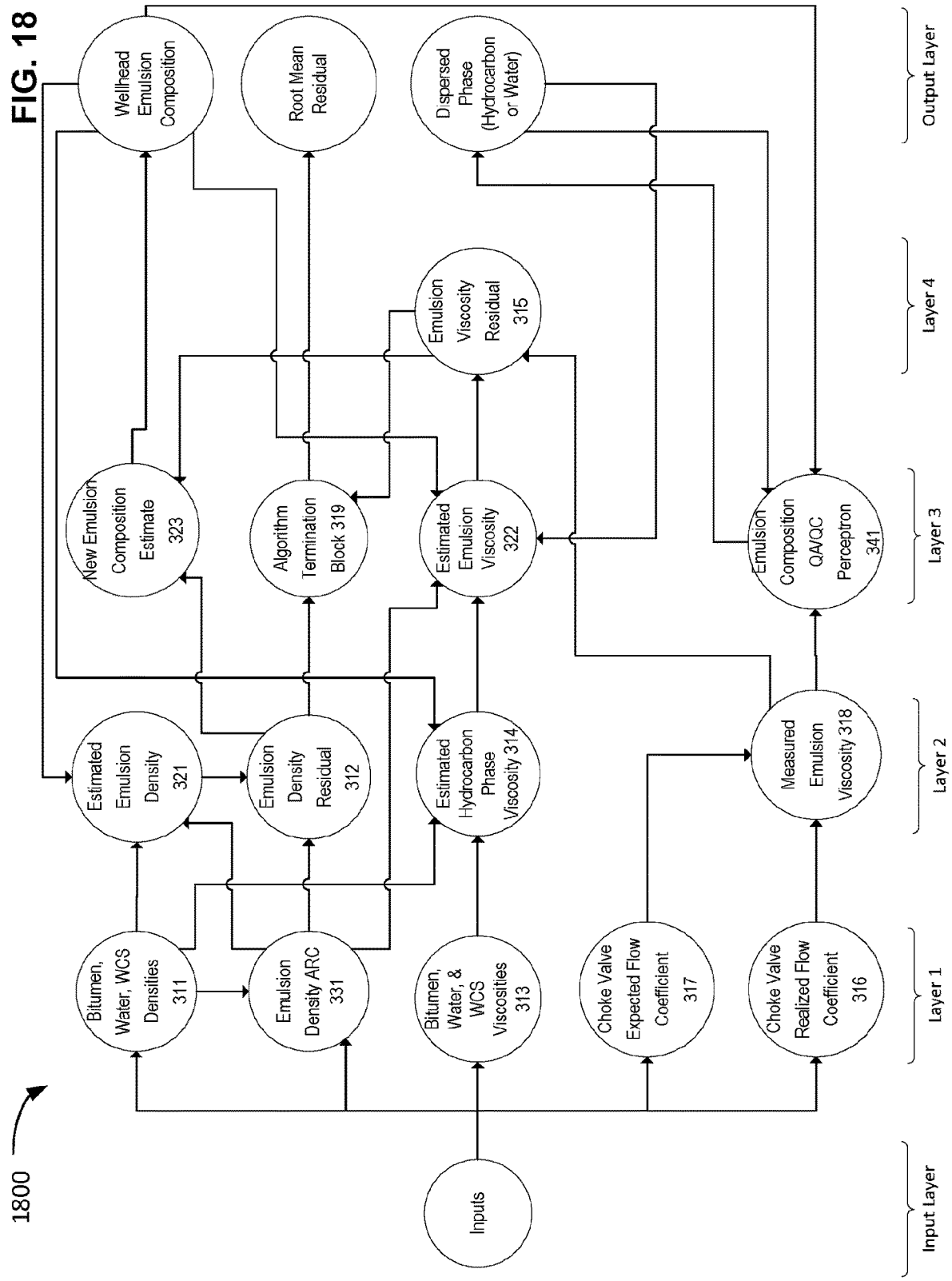
FIG. 18 is a flowchart illustrating layered aspects of an example neural network.

FIG. 18 shows aspects of an example neural network 1800 which can be used to sense or otherwise detect the composition of a produced fluid being conducted from a reservoir. In some embodiments, the nodes of the neural network correspond to the example process blocks illustrated in FIG. 3. In some embodiments, the input layer of the neural network includes a well's Electrical Submersible Pump (ESP) rotor speed; an injector well heel pressure; producer well heel and toe pressures; wellhead emulsion temperature; wellhead emulsion pressure; wellhead emulsion group separator pressure; wellhead emulsion flowrate; and wellhead emulsion choke valve stem travel.

In some embodiments, the output layer includes: wellhead emulsion composition (i.e. its water and bitumen concentrations); the neural network calculated density and viscosity combined error residual (i.e. its root mean residual); and an indication of whether water or oil constitutes the emulsion's dominant dispersed phase.

In some instances, neural networks may require significant computing power to produce accurate and high quality estimations. In some situations, limited computing resources may be available at a production location or in a process control system. In some embodiments, the neural network processes illustrated in FIG. 3 may be implemented as a gray-box neural network. In some instances, gray-box neural networks can include a combination of black-box neurons (i.e. statistical-only, small-scale mathematical models) and white-box neurons (i.e. small-scale mathematical models developed based on scientific relations between their inputs and outputs). In some instances, these neural networks may require significant computational resources during the training process.

In some embodiments, to reduce the training resource requirements, the neural network's training may be localized in the "Emulsion Composition QA/QC" Perceptron as Dispersed Phase Selection Matrix ≡ (134)

| Low Viscosity Level (Pa.s) | High Viscosity Level (Pa.s) | # of Water Successes | # of Hydrocarbon Successes | # of Total Failures |
|---|---|---|---|---|
| 0 | Low + 0.0002 | # | # | # |
| Previous Low + 0.0002 | Low + 0.0002 | # | # | # |
| 0.006 | 100 | # | # | # |

In some embodiments, the Perceptron both selects the dispersed phase and performs QA/QC on estimated emulsion composition data. Perceptron performs the first task by using the matrix described above and emulsion's measured viscosity to identify the emulsion's most probable dispersed phase. More specifically, perceptron matches emulsion's measured viscosity with one of the rows of this matrix and described herein (block 341). In some embodiments, the perceptron can be trained by developing a matrix of all of emulsion's dominant dispersed phases (i.e. one of the network's outputs) vs. all of viscosities calculated by the neuron as described with respect to block 318. With this approach, the training process can be simplified by focussing on the emulsion's dominant dispersed phase as the most weighted unknown variable in the neural network.

In some embodiments, the neural network can require less training by reducing accuracy for extreme cases which may not be fully modelled in the white-box neurons' core algorithms.

In some instances, since a large part of the neural network is based on white-box neurons means, it may requires less training than a traditional black-box neural network. In some embodiments, much of the training process can be localized at the "Emulsion Composition QA/QC" Perceptron. In some embodiments, this perceptron is trained dynamically using a recursive matrix which is filled by the network's output and part of its intermediate calculations as it processes additional data.

In some embodiments, the neural network 1800 can be represented as a network of approximately four layers. It should be noted that since the network is a combination of recurrent and feedforward networks, the neurons do not necessarily fall into distinct layers.

In some instances, true error can be calculated as a combination of meter measurement error, training error and model optimism. In some instances, preliminary results have shown that some embodiments of the systems and methods described herein generate outputs which are within 5% of water cut meter readings. Based on an approximate 5% measurement error in the industrial input devices, the true error can, in some scenarios, be estimated to be 10%.

In some instances, the methods and systems described herein may provide a reasonable alternative to current measurement and monitoring systems. In some embodiments, the methods and systems described herein may provide a backup system which may verify and/or monitor the outputs and/or the proper functioning of meters (such as water cut meters) in the system.

Although the embodiments have been described in detail, it should be understood that various changes, substitutions and alterations can be made herein without departing from the scope as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

As can be understood, the examples described above and illustrated are intended to be exemplary only. The scope is indicated by the appended claims.

The following table provides definitions for select symbols and abbreviations.

| Symbol | Description | Units |
|---|---|---|
| $A_{Droplet}$ | Emulsion Droplet Surface Area | $m^2$ |
| $A_{HC\ Droplet}$ | Emulsion Hydrocarbon Droplets' Surface Area | $m^2$ |
| $A_{Interface-Reference}$ | Emulsion Reference State Hydrocarbon-Water Interface Area | $m^2$ |
| $A_{Water\ Droplet}$ | Emulsion Water Droplets' Surface Area | $m^2$ |
| $A_o$ | Regression Coefficient | — |
| $A_1$ | Regression Coefficient | — |
| $A_2$ | Regression Coefficient | — |
| ARC | Advanced Regulatory Control | — |
| $B_o$ | Microsoft Excel Regression Coefficient | — |
| $B_1$ | Microsoft Excel Regression Coefficient | — |
| $C_1$ | Droplet Diameter Calculation Constant | — |
| $C_2$ | Droplet Diameter Calculation Constant | — |
| $C_v$ | Flow Coefficient | $USGPM.PSI^{-0.5}$ |
| $C_v$ (Expected) | Expected Flow Coefficient | $USGPM.PSI^{-0.5}$ |
| CNN | Convoluted Neural Network | — |
| $d_D$ | Emulsion Droplet Diameter | m |
| $d_{d-w}$ | Emulsion Water Droplet Diameter | m |
| DCS | Distributed Control Systems | — |
| DNN | Deep Neural Network | — |
| ESP | Electrical Submergible Pump | — |
| F | Flow Rate | $m^3/s$ |
| $F_V$ | Choke Valve Flow Coefficient Correction Factor | — |
| GN | Gauss-Newton | — |
| g | Gravity Constant | $m/s^2$ |
| $I\ (\Gamma, \kappa)$ | Yaron & Gal-Or Viscosity Model Emulsion Viscosity Correction Factor | — |
| i | Complex Number $\sqrt{-1}$ | — |
| $J_r$ | Gauss-Newton Algorithm Jacobean Matrix | — |
| $M_{HC}$ | Hydrocarbon Phase Molar Mass | kg/mol |
| $M_w$ | Water Molar Mass | kg/mol |
| MARP | Measurement, Recording, and Accounting Plan | — |
| NN | Neural Networks | — |
| $N_R$ | Wellhead Emulsion Choke Valve Reynolds Number | — |
| n | Regression Coefficient | — |
| P | Pressure | Pa |
| $P_{ESP\ Discharge}$ | ESP Discharge Pressure | Pa |
| PM | Preventive Maintenance | — |
| Q | Flow Rate | $m^3/hr$ |
| QA | Quality Control | — |
| QC | Quality Assurance | — |

-continued

| Symbol | Description | Units |
|---|---|---|
| $R(X'_j)$ | Gauss-Newton Algorithm Residual Vector (j algorithm) | — |
| $R_{Casing}$ | Producer Well Casing Radius | m |
| $R_{HC}$ | Emulsion Reference State Hydrocarbon Layer Depth | m |
| $R_{Production\ String}$ | Production String Radius | m |
| $R^2$ | Coefficient of Determination | — |
| $r_t(X_{j+1})$ | Gauss-Newton Algorithm Root Mean Residual | — |
| $r_1(X_j)$ | Gauss-Newton Algorithm Emulsion Density Residual | kg/m$^3$ |
| $r_2(X_j)$ | Gauss-Newton Algorithm Emulsion Viscosity Residual | Pa·s |
| $r_3(X_j)$ | Gauss-Newton Algorithm Emulsion Composition Residual | Pa·s |
| $r_4(X_j)$ | Gauss-Newton Algorithm Emulsion WCS Content Residual | Pa·s |
| $S_A$ | Emulsion Interfacial Entropy per Unit Area | J/m$^2$ |
| $S_{Emulsion}$ | Emulsion Interfacial Entropy | J/K |
| $S_{Reference}$ | Emulsion Reference State Interfacial Entropy | J/K |
| SAGD | Steam Assisted Gravity Drainage | — |
| T | Temperature | K |
| $V_{Droplet}$ | Emulsion Droplet Volume | m$^3$ |
| $V_{Eff}$ | Energy Dissipation Effective Volume | m$^3$ |
| $V_{HC}$ | Hydrocarbon Molar Volume | m$^3$/kg |
| $V_{Total}$ | Emulsion Total Volume | m$^3$ |
| $V_W$ | Water Molar Volume | m$^3$/kg |
| VBN | Refutas Method Viscosity Blend Number | — |
| $VBN_B$ | Refutas Method Bitumen Viscosity Blend Number | — |
| $VBN_{HC}$ | Refutas Method Hydrocarbon Phase Viscosity Blend Number | — |
| $VBN_{WCS}$ | Refutas Method WCS Viscosity Blend Number | — |
| $W_{HC\ Droplet-Final}$ | Emulsion Hydrocarbon Droplet Interfacial Enthalpy | J |
| $W_{Reference}$ | Emulsion Reference State Interfacial Enthalpy | J |
| $W_{Water\ Droplet-Final}$ | Emulsion Water Droplet Interfacial Enthalpy | J |
| WCS | Western Canadian Select | — |
| $X'_{j+1}$ | Emulsion Composition Vector (j + 1 iteration) | — |
| x | Microsoft Excel Regression Table Independent Variable | — |
| $x_{bitumen}$ & $x_B$ | Emulsion Bitumen Content | Mass Frac. |
| $x_{bitumen,j}$ | j$^{th}$ iteration emulsion bitumen content estimate | Mass Frac. |
| $x_{gas}$ | Emulsion Free Gas | — |
| $x_S$ | Emulsion solids content | Mass Frac. |
| $x_{water}$ & $x_W$ | Emulsion Water Content | Mass Frac. |
| $x_{water,j}$ | j$^{th}$ iteration emulsion water content estimate | Mass Frac. |
| $x_{WCS}$ | Emulsion Western Canadian Select Content | — |
| y | Microsoft Excel Regression Table Dependent Variable | — |
| $z_{ESP-TVD}$ | ESP True Vertical Depth | m |
| $\Gamma$ | Yaron & Gal-Or Viscosity Model Volume Fraction Parameter | — |
| $\Delta G_{IF}$ | Emulsion Interfacial Gibbs Free Energy Change | J |
| $\Delta S$ | Emulsion Interfacial Entropy Change | J/K |
| $\Delta W_{Water\ Droplet}$ | Emulsion Interfacial Water Droplet Enthalpy Change | J |
| $\Delta W_{HC\ Droplet}$ | Emulsion Interfacial Hydrocarbon Droplet Enthalpy Change | J |
| $\varepsilon$ | Turbulent Flow Energy Dissipation Rate | m$^2$/s$^3$ |
| $\kappa$ | Yaron & Gal-Or Viscosity Model Viscosity Parameter | — |
| $\mu$ | Dynamic Viscosity | Pa·s |
| $\mu_B$ | Bitumen Dynamic Viscosity | Pa·S |
| $\mu_{Continuous}$ | Emulsion Continuous Phase Viscosity | Pa·s |
| $\mu_{Dispersed}$ | Emulsion Dispersed Phase Viscosity | Pa·s |
| $\mu_{emulsion\ calculated}(X_j)$ | Emulsion Viscosity calculated from j$^{th}$ iteration's emulsion composition vector | Pa·s |
| $\mu_{emulsion\ measured}$ | Measured Emulsion Viscosity | Pa.s |
| $\mu_W$ | Water Dynamic Viscosity | Pa.s |
| $\nu$ | Kinematic Viscosity | — |
| $\nu_{HC}$ | Hydrocarbon Phase Kinematic Viscosity | — |
| $\varpi$ | Regression Coefficient | — |
| $\rho$ | Density | kg/m$^3$ |
| $\rho_{bitumen}$ | Reference Bitumen Density | kg/m$^3$ |
| $\rho_{emulsion}$ | Emulsion Density | kg/m$^3$ |
| $\rho_{emulsion\ calculated}(X_j)$ | Emulsion Density calculated from j$^{th}$ iteration's emulsion composition vector | kg/m$^3$ |
| $\rho_{Continuous}$ | Emulsion Continuous Phase Density | kg/m$^3$ |
| $\rho_{emulsion\ measured}$ | Measured Emulsion Density | kg/m$^3$ |
| $\rho_{HC}$ | Hydrocarbon Phase Density | kg/m$^3$ |

-continued

| Symbol | Description | Units |
|---|---|---|
| $\rho_{gas}$ | Emulsion Free Gas Density | kg/m³ |
| $\rho_S$ | Emulsion Solids Reference Density | kg/m³ |
| $\rho_{water}$ | Reference Water Density | kg/m³ |
| $\sigma_{HC}$ | Hydrocarbon Surface Tension | J/m² |
| $\sigma_W$ | Water Surface Tension | J/m² |
| $\sigma_{W\text{-}B}$ | Water-Bitumen Interfacial Tension | J/m² |
| $\sigma_{W\text{-}HC}°$ | Regression Coefficient | — |
| $\varsigma$ | Viscoelastic Emulsion Dynamic Viscosity Calculation Parameter | — |
| $\tau$ | Steam Density Calculation Intermediate Factor | — |
| $\gamma$ | Mass Fraction of Emulsion Water Existing as Droplets Suspended in Hydrocarbon Phase | Mass Frac. |
| $\phi_x$ | Volumetric Fraction of x in Emulsion | Vol. Frac. |
| $\phi_{Dispersed}$ | Emulsion Dispersed Phase Volumetric Fraction | Vol. Frac. |
| $\phi_0$ | Regression Coefficient | — |
| $\phi_1$ | Regression Coefficient | — |
| $\phi_2$ | Regression Coefficient | — |
| $\phi_3$ | Regression Coefficient | — |
| $\Psi$ | Viscoelastic Emulsion Dynamic Viscosity Calculation Parameter | — |
| $\Omega$ | Surface Tension Volume Factor | m/mol^(1/3) |

What is claimed is:

1. A system for sensing an estimated composition of a produced fluid being conducted from a reservoir, the system comprising:
   at least one device for measuring temperature data for the produced fluid;
   at least one device for obtaining flow rate data, pressure data, pump speed data and valve travel data for the produced fluid being conducted from the reservoir;
   at least one memory device for storing obtained and historical data;
   a first produced fluid density generator configured to:
      generate a first produced fluid density based at least in part on the obtained flow rate data, pressure data, and pump speed data for the produced fluid being conducted from the reservoir;
   a second produced fluid density generator configured to:
      generate a second produced fluid density based at least in part on a bitumen reference density corresponding to the measured temperature data, a water reference density corresponding to the measured temperature data, and a phantom component reference density corresponding to the measured temperature data; and
   a composition generator configured to:
      generate, with an iterative convergence tool, a phantom component content, a bitumen content and a water content for the produced fluid based on at least in part on: a material balance of the produced fluid and a difference between the first produced fluid density and the second produced fluid density; and
      generate outputs representing the phantom component content, the bitumen content and the water content.

2. The system of claim 1 comprising an alert generator configured to generate an alert signal when the water content meets a trigger condition.

3. The system of claim 1 comprising a water cut meter for measuring a water cut of the produced fluid being conducted from the reservoir; and a meter monitor configured to:
   compare the water cut with the phantom component content, the bitumen content and the water content; and
   generate alert signals when the comparison identifies a discrepancy between the water cut and the phantom component content, the bitumen content and the water content.

4. The system of claim 1, wherein the first produced fluid density generator is configured to generate a produced fluid contaminant indicator signal based on the first produced fluid density, a bitumen reference density corresponding to the measured temperature data and a water reference density corresponding to the measured temperature data; and
   wherein the second produced fluid density generator comprises a neural network configured to generate the second produced fluid density based in part on a neuron selected by the produced fluid contaminant indicator signal.

5. The system of claim 4, wherein the composition generator comprises a neural network configured to generate the phantom component content, the bitumen content and the water content based on the produced fluid contaminant indicator signal.

6. The system of claim 4, comprising an alert generator configured to generate an alert signal when the produced fluid contaminant indicator signal indicates that at least one of solids or gas is present the produced fluid.

7. The system of claim 1 comprising at least one device for measuring a produced fluid density;
   wherein generating the first produced fluid density comprises:
   generating a backup produced fluid density based at least in part on the obtained flow rate data, pressure data, and pump speed data; and
   selecting the measured produced fluid density as the first produced fluid density when the measured produced fluid density is within a density range between the water reference density corresponding to the measured temperature data and the bitumen reference density corresponding to the measured temperature data, or selecting the backup produced fluid density as the first produced fluid density when the measured produced fluid density is not within the density range.

8. The system of claim 1, wherein the iterative convergence tool adjusts the phantom component content until the material balance of the produced fluid and the difference between the first produced fluid density and the second produced fluid density converge.

9. The system of claim 1, comprising:
   at least one device for obtaining valve travel data for the produced fluid;

a first produced fluid viscosity generator configured to:
    generate a first produced fluid viscosity based at least in part on: the bitumen reference density and a bitumen reference viscosity corresponding to the measured temperature data, the water reference density and a water reference viscosity corresponding to the measured temperature data, and the phantom component reference density and a phantom component reference viscosity corresponding to the measured temperature data; and
a second produced fluid viscosity generator configured to:
    generate a second produced fluid viscosity based at least in part on the obtained valve travel data, pressure data and flow rate data;
wherein the composition generator is configured to generate, with the iterative convergence tool, the phantom component content, the bitumen content and the water content based on a difference between the first produced fluid viscosity and the second produced fluid viscosity.

10. The system of claim 9, wherein the first produced fluid viscosity generator comprises a neural network configured to generate the first produced fluid viscosity based in part on a neuron selected by a produced fluid contaminant indicator signal.

11. The system of claim 9, wherein the first produced fluid viscosity generator is configured to generate the first produced fluid viscosity based on a dispersed phase selection from a plurality of potential dispersed phases of the produced fluid.

12. The system of claim 11, comprising a perceptron configured to
    maintain a dispersed phase selection matrix based on previous selections by the perceptron; and
    generate the dispersed phase selection from the dispersed phase selection matrix based at least in part on the second produced fluid viscosity.

13. The system of claim 1, wherein the phantom component reference density is determined based on a Western Canadian Select crude density model.

14. A method for sensing an estimated composition of a produced fluid being conducted from a reservoir, the method comprising:
    measuring, with at least one sensing device, temperature data for the produced fluid;
    obtaining, with the at least one sensing device, flow rate data, pressure data, pump speed data and valve travel data for the produced fluid being conducted from the reservoir;
    generating a first produced fluid density based at least in part on the obtained flow rate data, pressure data, and pump speed data for the produced fluid being conducted from the reservoir;
    generating a second produced fluid density based at least in part on a bitumen reference density corresponding to the measured temperature data, a water reference density corresponding to the measured temperature data, and a phantom component reference density corresponding to the measured temperature data;
    generating, with an iterative convergence tool, a phantom component content, a bitumen content and a water content for the produced fluid based on at least in part on: a material balance of the produced fluid and a difference between the first produced fluid density and the second produced fluid density; and
    generating outputs representing the phantom component content, the bitumen content and the water content.

15. The method of claim 14 comprising: comparing a water cut output from a water cut meter measuring the water cut of the produced fluid being conducted from the reservoir with the phantom component content, the bitumen content and the water content; and
    generating alert signals when the comparison identifies a discrepancy between the water cut and the phantom component content, the bitumen content and the water content.

16. The method of claim 14, comprising generating a produced fluid contaminant indicator signal based on the first produced fluid density, a bitumen reference density corresponding to the measured temperature data and a water reference density corresponding to the measured temperature data; and
    generating the second produced fluid density based in part on a neuron selection within a neural network and based on the produced fluid contaminant indicator signal.

17. The method of claim 14 comprising measuring, with the at least one sensing device, a produced fluid density; and
    wherein generating the first produced fluid density comprises:
    generating a backup produced fluid density based at least in part on the obtained flow rate data, pressure data, and pump speed data; and
    selecting the measured produced fluid density as the first produced fluid density when the measured produced fluid density is within a density range between the water reference density corresponding to the measured temperature data and the bitumen reference density corresponding to the measured temperature data, or selecting the backup produced fluid density as the first produced fluid density when the measured produced fluid density is not within the density range.

18. The method of claim 14, comprising adjusting, with the iterative convergence tool, the phantom component content until the material balance of the produced fluid and the difference between the first produced fluid density and the second produced fluid density converge.

19. The method of claim 14, comprising:
    obtaining valve travel data for the produced fluid;
    generating a first produced fluid viscosity based at least in part on: the bitumen reference density and a bitumen reference viscosity corresponding to the measured temperature data, the water reference density and a water reference viscosity corresponding to the measured temperature data, and the phantom component reference density and a phantom component reference viscosity corresponding to the measured temperature data;
    generating a second produced fluid viscosity based at least in part on the obtained valve travel data, pressure data and flow rate data; and
    generating, with the iterative convergence tool, the phantom component content, the bitumen content and the water content based on a difference between the first produced fluid viscosity and the second produced fluid viscosity.

20. A non-transitory, computer-readable medium or media having stored thereon instructions which when executed by at least one processor configure the at least one processor for:
    measuring, with at least one sensing device, temperature data for the produced fluid;

obtaining, with the at least one sensing device, flow rate data, pressure data, pump speed data and valve travel data for the produced fluid being conducted from the reservoir;

generating a first produced fluid density based at least in part on the obtained flow rate data, pressure data, and pump speed data for the produced fluid being conducted from the reservoir;

generating a second produced fluid density based at least in part on a bitumen reference density corresponding to the measured temperature data, a water reference density corresponding to the measured temperature data, and a phantom component reference density corresponding to the measured temperature data;

generating, with an iterative convergence tool, a phantom component content, a bitumen content and a water content for the produced fluid based on at least in part on: a material balance of the produced fluid and a difference between the first produced fluid density and the second produced fluid density; and generating outputs representing the phantom component content, the bitumen content and the water content.

* * * * *